(12) United States Patent
Reguera et al.

(10) Patent No.: US 8,729,233 B2
(45) Date of Patent: May 20, 2014

(54) MICROBIAL NANOWIRES AND PRODUCTS RELATED THERETO

(75) Inventors: Gemma Reguera, Lansing, MI (US); Stuart Tessmer, Okemos, MI (US); Joshua Veazey, Pittsburgh, PA (US); Sanela Lampa-Pastirk, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 13/221,459

(22) Filed: Aug. 30, 2011

(65) Prior Publication Data

US 2012/0053320 A1 Mar. 1, 2012

Related U.S. Application Data

(60) Provisional application No. 61/378,188, filed on Aug. 30, 2010, provisional application No. 61/378,240, filed on Aug. 30, 2010.

(51) Int. Cl.
*C07K 1/00* (2006.01)
*C07K 14/00* (2006.01)

(52) U.S. Cl.
USPC .......................................... 530/350; 530/412

(58) Field of Classification Search
None
See application file for complete search history.

(56) References Cited

U.S. PATENT DOCUMENTS 5,418,140 A * 5/1995 Chang et al. .................. 435/7.32
5,968,769 A * 10/1999 Green et al. .................. 435/69.1
7,498,155 B2 3/2009 Lovley et al.

FOREIGN PATENT DOCUMENTS

JP 2010033344 A 2/2010
WO 2006096821 9/2006

OTHER PUBLICATIONS

Cory, Rose, et al., "Fluorescence Spectroscopy Reveals Ubiquitous Presence of Oxidized and Reduced Quinones in Dissolved Organic Matter", Environ. Sci. Technol., vol. 39., No. 21, (2005), 8142-8149.
Craig, Lisa, et al., "Type IV Pilus Structure by Cryo-Electron Microscopy and Crystallography: Implications for Pilus Assembly and Functions", Molecular Cell 23, (Sep. 1, 2006), 651-662.
Hay, Sam, et al., "Protein Engineering of Cytochrome b562 for Quinone Binding and Light-Induced Electron Transfer", PNAS, vol. 101, No. 51, (Dec. 21, 2004), 17675-17680.
Leang, Ching, et al., "Alignment of the c-Type Cytochrome OmcS Along Pili of Geobacter sulferreducens", AEM Accepts, published online ahead of print on Apr. 16, 2010, 1-17.

U.S. Appl. No. 13,221,495 Office Action mailed on Mar. 13, 2013.
International Application No. PCT/US2012/053221 International Search Report mailed on Apr. 25, 2013.
Cologgi 2011 "Extracellular reduction of uranium via Geobacter conductive pili as a protective cellular mechanism" Environmental Science PNAS Early Edition www.pnas.org/cgi/content/short/1108616108.
Forero 2011 "Properties and Applications of Self-Assembled Biomolecules Innanostructred Biomimetic Interfaces" Michicgan State University.
Methe 2003 "Genome of Geobacter sulfurreducen: Metal Reduction in Subsurface Environments" Science 302, 1967.
U.S. Appl. No. 13/221,495 Non-Final Rejection mailed on Jul. 12, 2013.
Aklujkar, Muktak et al. "The genome sequence of Geobacter metallireducens: features of metabolism, physiology and regulation common and dissimilar to Geobacter sulfurreducens" BMC Microbiology May 27, 2009, 9:109.
Chothia, Cyrus et al. "The relation between the divergence of sequence and structure in proteins" The EMBO Journal vol. 5, No. 4 pp. 823-826, 1986.
Mikayama, Toshifumi et al. "Molecular cloning and functional expression of a cDNA encoding glycosylation-inhibiting factor" PNAS USA vol. 90 pp. 10056-10060, Nov. 1993.
Rudinger, J. et al. "Characteristics of the amino acids as components of a peptide hormone sequence" National Institute for Medical Research, Jun. 1976.
Collinson et al., "Purification and Characterization of Thin, Aggregative Fimbriae from *Salmonella enteritidis*", Journal of Bacteriology, vol. 173, No. 15, Aug. 1991, pp. 4773-4781.
Feliciano et al., "Molecular and Electronic Structure of the Peptide Subunit of Geobacter Sulfurreducens Conductive Pili from First Principles", The Journal of Physical Chemistry A, vol. 116, No. 30, Jul. 10, 2012, pp. 8023-8030.
Nagarajan et al., "De Novo Assembly of the Complete Genome of an Enhanced Electricity-Producing Variant of Geobacter sulfurreducens Using Only Short Reads", PLoS ONE, vol. 5, No. 6, e10922, Jun. 2010, pp. 1-9.
Reguera et al., "Extracellular Electron Transfer via Microbial Nanowires", Nature, vol. 435, Jun. 23, 2005, pp. 1098-1101.
Veazey et al., "Microbial Nanowire Electronic Structure Probed by Scanning Tunneling Microscopy", Biophysical Journal, vol. 98, No. 3, S1, Biophysical Society, Jan. 2010, pp. 565a.
Yang et al., "Metabolic Response of Geobacter Sulfurreducens towards Electron Donor/Acceptor Variation", Microbial Cell Factories, vol. 9, No. 90, 2010, pp. 1-15.

* cited by examiner

*Primary Examiner* — Albert Navarro
(74) *Attorney, Agent, or Firm* — Clark IP Law, PLC

(57) ABSTRACT

A nanowire comprising a purified protein filament, such as a pilus, isolated from a bacterium, such as *Geobacter sulfurreducens*, is provided. Such a purified pilus can contain peptide subunits capable of assembling into the protein filament and establishing an electrical connection with an insoluble electron acceptor. The novel nanowires can be produced via a novel single step. Such nanowires are useful in applications requiring rectifying behavior.

17 Claims, 17 Drawing Sheets
(8 of 17 Drawing Sheet(s) Filed in Color)

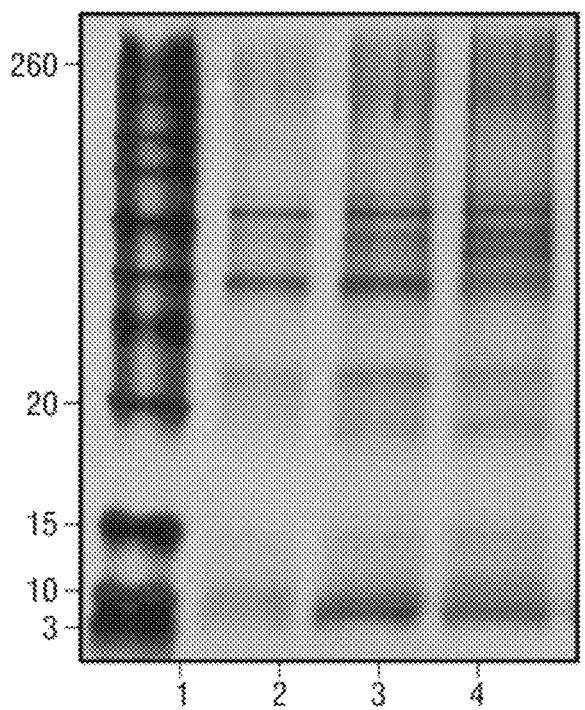 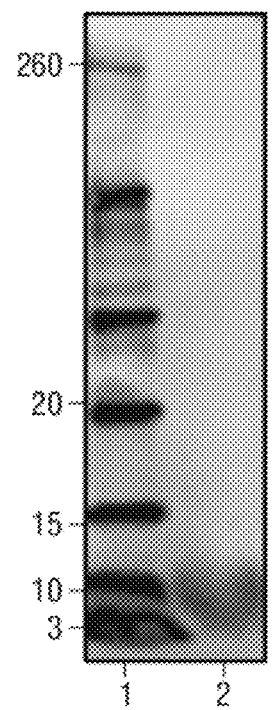
*FIG. 3A*          *FIG. 3B*
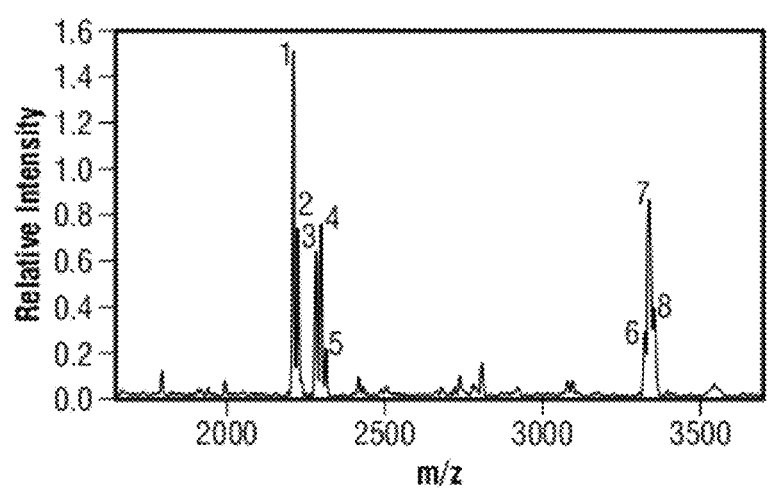
*FIG. 4*

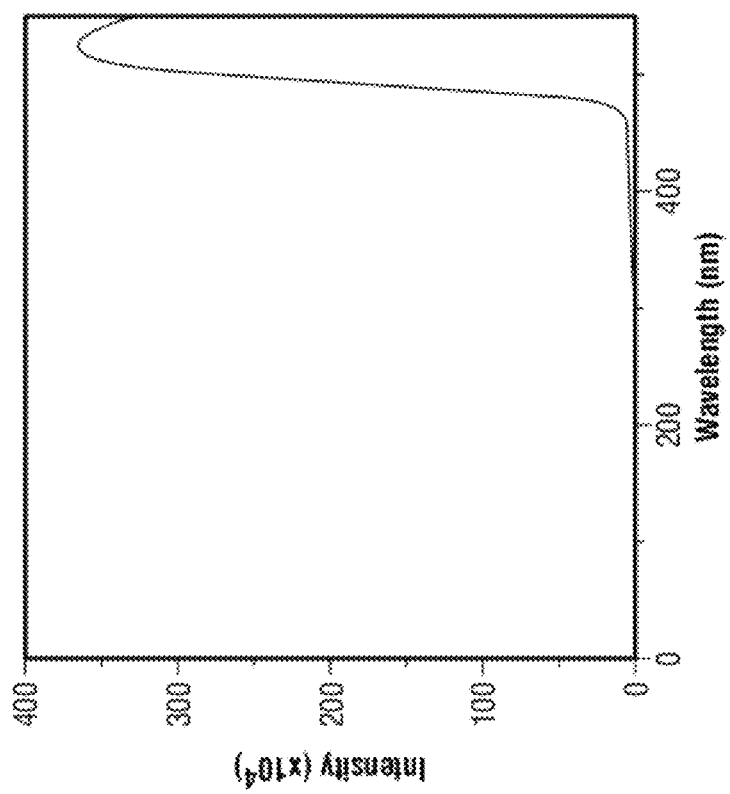

SEQUENCE LISTING

```
<160> NUMBER OF SEQ ID NOS: 18

<210> SEQ ID NO 1
<211> LENGTH: 61
<212> TYPE: PRT
<213> ORGANISM: Geobacter sulfurreducens

<400> SEQUENCE: 1

Phe Thr Leu Ile Glu Leu Leu Ile Val Val Ala Ile Ile Gly Ile Leu
 1               5                  10                  15

Ala Ala Ile Ala Ile Pro Gln Phe Ser Ala Tyr Arg Val Lys Ala Tyr
            20                  25                  30
```

Asn Ser Ala Ala Ser Ser Asp Leu Arg Asn Leu Lys Thr Ala Leu Glu
            35                  40                  45

Ser Ala Phe Ala Asp Asp Gln Thr Tyr Pro Pro Glu Ser
    50                  55                  60

<210> SEQ ID NO 2
<211> LENGTH: 18
<212> TYPE: PRT
<213> ORGANISM: Geobacter sulfurreducens

<400> SEQUENCE: 2

Lys Thr Ala Leu Glu Ser Ala Phe Ala Asp Asp Gln Thr Tyr Pro Pro
1               5                   10                  15

Glu Ser

<210> SEQ ID NO 3
<211> LENGTH: 18
<212> TYPE: PRT
<213> ORGANISM: Geobacter sulfurreducens

<400> SEQUENCE: 3

Lys Thr Ala Leu Glu Ser Ala Phe Ala Asp Asp Gln Thr Tyr Pro Pro
1               5                   10                  15

Glu Ser

<210> SEQ ID NO 4
<211> LENGTH: 21
<212> TYPE: PRT
<213> ORGANISM: Geobacter sulfurreducens

<400> SEQUENCE: 4

Arg Asn Leu Lys Thr Ala Leu Glu Ser Ala Phe Ala Asp Asp Gln Thr
1               5                   10                  15

Tyr Pro Pro Glu Ser
            20

<210> SEQ ID NO 5
<211> LENGTH: 21
<212> TYPE: PRT
<213> ORGANISM: Geobacter sulfurreducens

<400> SEQUENCE: 5

Arg Asn Leu Lys Thr Ala Leu Glu Ser Ala Phe Ala Asp Asp Gln Thr
1               5                   10                  15

Tyr Pro Pro Glu Ser
            20

<210> SEQ ID NO 6
<211> LENGTH: 21
<212> TYPE: PRT
<213> ORGANISM: Geobacter sulfurreducens

<400> SEQUENCE: 6

Arg Asn Leu Lys Thr Ala Leu Glu Ser Ala Phe Ala Asp Asp Gln Thr
1               5                   10                  15

Tyr Pro Pro Glu Ser
            20

<210> SEQ ID NO 7
<211> LENGTH: 32
<212> TYPE: PRT
<213> ORGANISM: Geobacter sulfurreducens -continued

```
<400> SEQUENCE: 7

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Val
            20                  25                  30

<210> SEQ ID NO 8
<211> LENGTH: 32
<212> TYPE: PRT
<213> ORGANISM: Geobacter sulfurreducens

<400> SEQUENCE: 8

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Val
            20                  25                  30

<210> SEQ ID NO 9
<211> LENGTH: 32
<212> TYPE: PRT
<213> ORGANISM: Geobacter sulfurreducens

<400> SEQUENCE: 9

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Val
            20                  25                  30

<210> SEQ ID NO 10
<211> LENGTH: 71
<212> TYPE: PRT
<213> ORGANISM: Geobacter sulfurreducens

<400> SEQUENCE: 10

Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Val Lys Ala Tyr Asn Ser Ala Ala Ser Ser
        35                  40                  45

Asp Leu Arg Asn Leu Lys Thr Ala Leu Glu Ser Ala Phe Ala Asp Asp
    50                  55                  60

Gln Thr Tyr Pro Pro Glu Ser
65                  70

<210> SEQ ID NO 11
<211> LENGTH: 71
<212> TYPE: PRT
<213> ORGANISM: Geobacter sulfurreducens

<400> SEQUENCE: 11

Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Val Lys Ala Tyr Asn Ser Ala Ala Ser Ser
        35                  40                  45

Asp Leu Arg Asn Leu Lys Thr Ala Leu Glu Ser Ala Phe Ala Asp Asp
    50                  55                  60
```

```
Gln Thr Tyr Pro Pro Glu Ser
 65                  70

<210> SEQ ID NO 12
<211> LENGTH: 70
<212> TYPE: PRT
<213> ORGANISM: Geobacter lovleyi

<400> SEQUENCE: 12

Met Leu Asn Lys Ile Arg Asn Arg Lys Gly Phe Thr Leu Ile Glu Leu
 1               5                  10                  15

Leu Ile Val Val Ala Ile Ile Gly Ile Leu Ala Ala Val Ala Ile Pro
            20                  25                  30

Gln Phe Thr Thr Tyr Arg Ile Lys Gly Tyr Asn Ser Asn Ala Thr Ser
        35                  40                  45

Asp Leu Arg Asn Leu Lys Thr Val Leu Glu Ser Val Phe Ala Asp Arg
    50                  55                  60

Gln Gly Tyr Pro Gly Ser
 65                  70

<210> SEQ ID NO 13
<211> LENGTH: 74
<212> TYPE: PRT
<213> ORGANISM: Pelobacter propionicus

<400> SEQUENCE: 13

Met Leu Asn Lys Leu Arg Asn Arg Lys Gly Phe Thr Leu Ile Glu Leu
 1               5                  10                  15

Leu Ile Val Val Ala Ile Ile Gly Ile Leu Ala Ala Ile Ala Ile Pro
            20                  25                  30

Gln Phe Ser Ala Tyr Arg Ala Lys Ala Tyr Asn Ser Ala Ala Asn Ser
        35                  40                  45

Asp Leu Lys Asn Ile Lys Thr Gly Met Glu Ala Phe Met Ala Asp Asn
    50                  55                  60

Gln Gln Tyr Pro Gly Asp Val Asp Tyr Arg
 65                  70

<210> SEQ ID NO 14
<211> LENGTH: 69
<212> TYPE: PRT
<213> ORGANISM: Geobacter metallireducens

<400> SEQUENCE: 14

Met Leu Gln Lys Leu Arg Asn Lys Lys Gly Phe Thr Leu Ile Glu Leu
 1               5                  10                  15

Leu Ile Val Val Ala Ile Ile Gly Ile Leu Ala Ala Ile Ala Ile Pro
            20                  25                  30

Gln Phe Ala Ala Tyr Arg Gln Lys Ala Phe Asn Ser Ala Ala Glu Ser
        35                  40                  45

Asp Leu Lys Asn Thr Lys Thr Asn Leu Glu Ser Tyr Tyr Ser Glu His
    50                  55                  60

Gln Phe Tyr Pro Asn
 65
```

```
<210> SEQ ID NO 15
<211> LENGTH: 74
<212> TYPE: PRT
<213> ORGANISM: Geobacter sp.

<400> SEQUENCE: 15

Met Leu Asn Lys Leu Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Ala Lys Ala Tyr Asn Ser Ala Ala Asn Ser
        35                  40                  45

Asp Leu Lys Asn Met Lys Thr Gly Met Glu Ala Tyr Met Ala Asp Arg
    50                  55                  60

Gln Ala Tyr Pro Ala Leu Leu Asp Gln Arg
65                  70

<210> SEQ ID NO 16
<211> LENGTH: 76
<212> TYPE: PRT
<213> ORGANISM: Geobacter bemidjiensis

<400> SEQUENCE: 16

Met Leu Asn Lys Leu Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Glu Lys Ala Tyr Asn Ala Ala Ser Asn Ser
        35                  40                  45

Asp Leu Lys Asn Phe Lys Thr Gly Leu Glu Ala Phe Asn Ala Asp Phe
    50                  55                  60

Gln Thr Tyr Pro Ala Ala Tyr Val Ala Ser Thr Asn
65                  70                  75

<210> SEQ ID NO 17
<211> LENGTH: 74
<212> TYPE: PRT
<213> ORGANISM: Geobacter sp.

<400> SEQUENCE: 17

Met Leu Asn Lys Ile Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Ala Lys Ala Tyr Asn Ala Ala Ala Asn Ser
        35                  40                  45

Asp Leu Lys Asn Ile Lys Thr Gly Met Glu Ala Tyr Met Ala Asp Arg
    50                  55                  60

Gln Ala Tyr Pro Val Ser Leu Asp Glu Arg
65                  70

<210> SEQ ID NO 18
<211> LENGTH: 74
<212> TYPE: PRT
<213> ORGANISM: Geobacter sp.

<400> SEQUENCE: 18

Met Leu Asn Lys Ile Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
```

```
                     20                  25                  30

Gln Phe Ser Ala Tyr Arg Ala Lys Ala Tyr Asn Ala Ala Asn Ser
        35                  40                  45

Asp Leu Lys Asn Ile Lys Thr Gly Met Glu Ala Tyr Met Ala Asp Arg
    50                  55                  60

Gln Ala Tyr Pro Val Ser Leu Asp Glu Arg
65                  70
```

MICROBIAL NANOWIRES AND PRODUCTS RELATED THERETO

This application claims the benefit under 35 U.S.C. 119(e) of the filing dates of U.S. Provisional Application Ser. Nos. 61/378,188 and 61/378,240, both filed on Aug. 30, 2010, both of which are hereby incorporated by reference in their entireties.

STATEMENT OF GOVERNMENT RIGHTS

This invention was made with government support under R01 ES017052 awarded by the National Institutes of Health and MCB1021948 awarded by the National Science Foundation. The government has certain rights in this invention.

BACKGROUND

Electron transfer through proteins is the core process of all of energy transduction pathways in living cells. While metals and cofactors have for long been known to be key determinants of protein redox activity, only more recently has it been demonstrated that individual amino acids directly contribute to intramolecular and intermolecular electron transfer reactions.

SUMMARY

Novel microbial nanowires (e.g., "nanowires") and methods of making and using same are described herein. In one embodiment, a nanowire is provided, which comprises a purified protein filament, such as a pilus, isolated from a bacterium, such as Geobacteraceae, the purified pilus containing peptide subunits capable of assembling into the protein filament and establishing an electrical connection with an insoluble electron acceptor. The insoluble electron acceptor can include, but is not limited to, Fe(III) oxide minerals, an electrode, a second purified pilus, and combinations thereof.

In one embodiment, a method is provided which comprises lysing a bacterium containing pili; the pili containing a target protein; removing debris from the pili; and separating non-target proteins from the pili to produce purified pili at high yields, such as at least 63%. In one embodiment, the lysing, removing and separating steps occur at substantially the same time. In some embodiments, the target protein is a peptide subunit or a pilin subunit. The purified pili may, in one embodiment, be formed by polymerization of pilin subunits via hydrophobic interactions. Non-target proteins include, but are not limited to adsorbed proteins, bound proteins, unbound proteins or combinations thereof. The novel methods described herein separate microbial nanowires from other cellular components, enabling its enrichment and concentration in pure form.

In one embodiment, the Geobacteraceae is *Geobacter sulfurreducens*. The pilin subunits can self-assemble into nanowires that can include one or more nanowire polypeptide subunits with various molecular weights (MWs). The subunits can have a variety of molecular weights ranging from, for example, at least about 3-kDa, or higher, or between about 3-kDa and about 25-kDa or between about 3-kDa and 20-kDa or between about 3-kDa and about 10-kDa or between about 4-kDa and about 9-kDa, or between about 5.5-kDa and about 7.5-kDa, including any range there between. In one embodiment, the subunit MW is about 6.5-kDa or at least about 6.5-kDa. In one embodiment, such nanowires do not contain metals, contaminating proteins, ions and other known redox cofactors such as flavins and quinones.

In one embodiment, a rectifier comprising one or more nanowires, each comprising a protein filament, such as a pilus isolated from a bacterium, the protein filament containing peptide subunits capable of assembling into the protein filament and establishing an electrical connection with an insoluble electron acceptor, is provided. In one embodiment, each of the peptide subunits is the same type of protein. For example, the peptide subunits can be *Geobacter sulfurreducens* pilin subunits.

In one embodiment, the rectifiers described herein are capable of functioning as an asymmetric conductor for voltages of various ranges, such as, for example, voltages (V) having a range of about $\pm 0.8$ V or a range of about $\pm 1.2$ V. The rectifiers may further be useful at higher voltages, although if the voltage is too high, excessive heat and damage to the rectifier and/or associated materials may occur, thus reducing the performance of the one or more nanowires contained therein.

Such rectifiers are expected to be useful in many fields and, in one embodiment, are adapted for use in radio demodulation, low voltage AC-DC power conversion, current steering, power switches, over voltage protection, logic circuitry in electronic devices or computer chips.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and 3B show protein composition of purified pili according to various embodiments.

FIG. 4 is a Matrix-Assisted Laser Desorption/Ionization-Time of Flight (MALDI-TOF) mass spectrometry spectrum of tryptic peptides from the 7-kDa protein band electrophoretically separated after depolymerizing purified pili with 2% octyl-glucoside according to an embodiment.

FIG. 15C shows a fluorescence spectrum of a riboflavin standard solution in isopropanol.

FIG. 16 shows the SEQ ID NO:1 amino acid sequence of the nanowire pilin subunit of *Geobacter sulfurreducens* according to an embodiment. The locations of the conserved tyrosine residues (Y) are identified with black shading while the negatively charged amino acids aspartic acid and glutamic acid (D and E, respectively) are identified with underlining and the positively charged amino acids lysine, arginine and histidine (K, R, and H, respectively) are identified with grey shading.

DETAILED DESCRIPTION

In the following detailed description of embodiments of the invention, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

The term "rectifier" as used herein, refers to one or more nanoscale solid-state electronic diodes that act as either a conductor or an insulator, depending on the sign of the voltage. A rectifier provides asymmetric axial electronic conductance, i.e., differential forward versus reverse conductivity. A single diode and rectifier essentially refer to the same type of component. By combining more than one diode together, various properties of the rectifier can be altered.

The novel pure nanowires described herein contain substantially all pili with little to no debris. A novel method of making the pure nanowires as well as a novel use for the pure nanowires as rectifiers is also provided.

Bacteria, such as Geobacteraceae bacteria, can be used to produce non-pure protein filaments. U.S. Pat. No. 7,498,155 to Lovley, for example, describes preparation of non-pure protein filaments, which can also be referred to as non-pure microbial or non-pure pilus nanowires, from bacteria, by using mechanical shearing. However, this method also shears off components of the cell's exterior, thus contaminating the resulting product with cellular materials to produce non-pure nanowires containing very few pili and a majority of insulating cellular debris.

Figure 1:
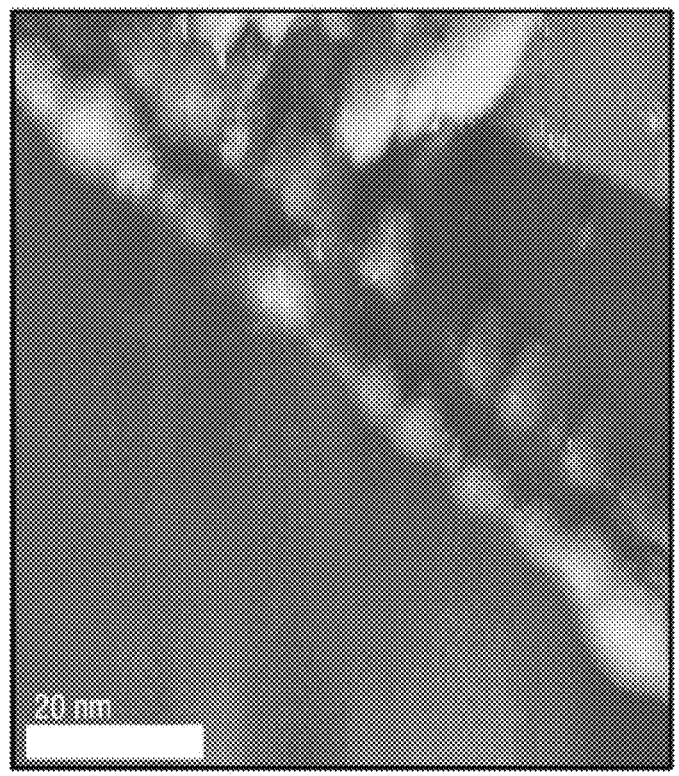
FIG. 1 shows a prior art scanning tunnel microscopy (STM) image of a non-pure pilus nanowire *G. sulfurreducens* in situ.

Additionally, these non-pure nanowires are known to have cytochromes (i.e., metalloproteins) which align along the non-pure nanowire, thus masking any diode behavior (if present). See, for example, FIG. 1, which shows a prior art STM image of a non-pure pilus nanowire of *G. sulfurreducens* located on a surface of a cleaved highly oriented pyrolytic graphite (HOPG) substrate. The double image of the pilus is the result of a double tip that developed while scanning this region. The upper center region shows what may be additional pili overlapping with the featured pilus (V=−1 V, I=−70 pA) may also be present. Such non-pure nanowires cannot function as, and are not, diodes. Conventional thinking also suggests that, even if non-pure nanowires could be purified, they would not show rectifying behavior, as such nanowires are thought to be associated with metals or metalloenzymes. At best, it has been theorized that these non-pure nanowires may exhibit ohmic behavior. As such, the prior art non-pure nanowires are limited to applications requiring only symmetric conductance, such as passive electrical connections between active nanoelectronic components.

Surprisingly, and in contrast to conventional thinking, the inventors are the first to not only produce novel purified microbial nanowires (hereinafter "nanowires" or "purified nanowires"), but to also demonstrate the ability of these novel products to conduct electrons along their length and to function as rectifiers. In one embodiment, the protein matrix can conduct electrons axially and at rates several orders of magnitude above those measured during the respiration of Fe(III) oxides. These distances and rates greatly exceed the known limits for charge transport reactions through protein matrices. As such, the pilus nanowires represent a new paradigm in protein electron transfer. The novel purified nanowires described herein are therefore expected to be useful in a variety of applications as described below.

As noted above, the purified nanowires described herein contain substantially all pili with little to no debris. As such, the pili can be isolated or purified. In one embodiment, the pili have been stripped from adsorbed or bound proteins. Debris, if present, can be identified as extra bands in depolymerized samples. The pili are oligomeric forms (e.g., dimmers, trimers, tetramers, etc.) of peptide subunits. One type of peptide subunit that can be used to form the pili is a Geobacteraceae pilin subunit.

Geobacteraceae bacteria naturally produce protein filaments known as pili that are electrically conductive. For this reason, they are generally referred to as microbial or pilus nanowires. The pilus nanowires are protein filaments assembled on the cell envelope through the polymerization via hydrophobic interactions of a single peptide subunit, the pilin or PilA. The purified pili are electrically conductive. As the pili protrude outside the cell, other proteins, such as metalloproteins known as c-cytochromes, can bind the pili and may contribute to their conductivity and adhesive properties. However, biochemical analyses of the purified pilin subunits have demonstrated that they were not directly associated with metals or metalloenzymes even when they assemble into nanowires. Furthermore, they lack any biological redox cofactors such as flavins and quinones. Thus, the conductivity of the pilin subunits is intrinsic to the nanowire protein filament and is not due to any redox-active component that may associate with the nanowire polypeptide, such as metals, ions, contaminants, metalloenzymes, flavins or quinones.

The peptide subunit (or pilin) in the electrically conductive pili is encoded by the pilA gene of Geobacteraceae bacteria. The product of the pilA gene generates a peptide or PilA or pilin that polymerizes via hydrophobic interactions to form the pilus. The Geobacteraceae pilus nanowire electrically connects the cell with electron acceptors in its environment. This electronic connection enables the cell to gain energy through the transfer of metabolically-generated electrons across electron transport proteins, such as c-cytochromes and other metalloproteins of the cell envelope, and through the pilus. The pilus serves as the main electrical connection between the cell and extracellular acceptors such as Fe(III) oxides. *Geobacter sulfurreducens* is naturally found in underground sediment where anaerobic conditions may require that an electron acceptor other than oxygen be employed and where minerals or other electron acceptors are commonly available. Thus, although *Geobacter sulfurreducens* can utilize oxygen as an electron acceptor, these bacteria can also transfer electrons from their pili to extracellular electron acceptors such as Fe(III) oxides, resulting in insoluble Fe(III) in the environment to be reduced to soluble Fe(II).

Figure 2A:
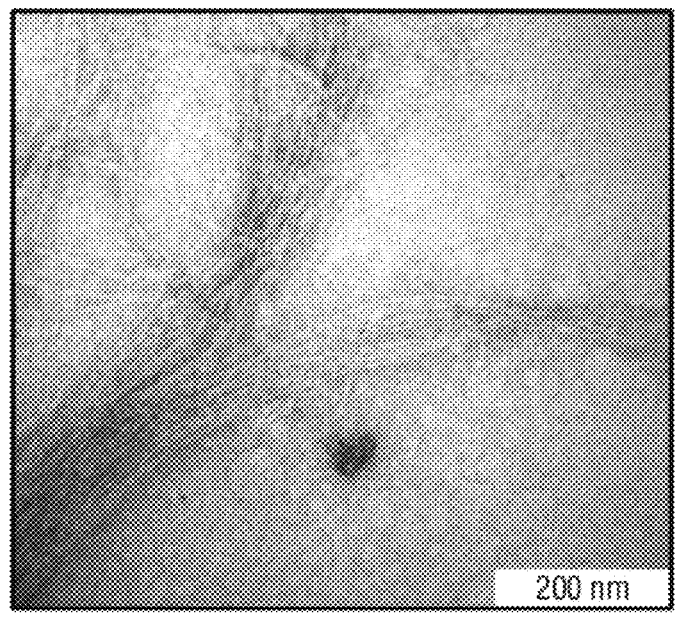
FIG. 2A is a Transmission Electron Microscopy (TEM) micrograph of negatively-stained purified pili of *G. sulfurreducens* according to an embodiment.

The pilus nanowires are dynamic filaments that protrude and retract by polymerizing and depolymerizing the pilin subunits at the cell envelope. Thus, several pilin peptides are assembled to make a pilus that can function as a nanowire. Extension and retraction events are powered, respectively, by the PilB (pilin polymerase) and PilT (pilin depolymerase) proteins, which belong to the secretion NTPase superfamily. The pilus nanowires are predominantly helical (FIG. 2) in structure. In particular, they are composed of an α-helical core spanning the hydrophobic N-terminus region that promotes pilin polymerization, and a short αβ-loop in the C-terminal region. Thus, they lack the long αβ-loop and extensive C-terminal globular head that other bacterial pili possess.

Pilin assembly occurs via hydrophobic interactions proceeding in a helical fashion that may help position electroactive amino acids by merging or bonding their atomic orbitals optimally so as to favor charge transport along and across the nanowire.

Different species of Geobacteraceae exist and can be used to produce nanowire protein filaments. Such Geobacteraceae species can produce pilin subunits (or PilA subunits) that have somewhat different amino acid sequences. Pilin subunits are selected that assemble into protein filaments and are capable of establishing an electrical connection with an insoluble electron acceptor.

In one embodiment, the pilin subunit can be from *Geobacter sulfurreducens*. An example of a pilin subunit sequence from *Geobacter sulfurreducens* is shown in FIG. 16 (SEQ ID NO:1) (see also, Example 1). Such a pilin subunit can have additional amino acids at the N-terminal or C-terminal end. For example, the pilin subunit can have a signal sequence as is shown below for the full length amino acid sequence of the pilin PilA from *Geobacter sulfurreducens* (SEQ ID NO:10).

```
  1 MLQKLRNRKG FTLIELLIVV AIIGILAAIA IPQFSAYRVK

41 AYNSAASSDL RNLKTALESA FADDQTYPPE S
```

In other embodiments, the pilin subunit can have any of SEQ ID NO:11-18 described below Amino acids 20-90 of the *Geobacter sulfurreducens* PCA nanowire PilA with sequence accession number NP_952547.1 (gi: 39996596) has the following sequence (SEQ ID NO:11).

```
  1 MLQKLRNRKG FTLIELLIVV AIIGILAAIA IPQFSAYRVK

41 AYNSAASSDL RNLKTALESA FADDQTYPPE S
```

The Type IV pilin PilA from *Geobacter sulfurreducens* KN400 having sequence accession number ADI84335.1 (gi: 298505612) has the following sequence (SEQ ID NO:12).

```
  1 MLQKLRNRKG FTLIELLIVV AIIGILAAIA IPQFSAYRVK

41 AYNSAASSDL RNLKTALESA FADDQTYPPE S
```

The pilin domain-containing protein *Geobacter lovleyi* SZ having sequence accession number YP_001952332.1 (gi: 189425155) has the following sequence (SEQ ID NO:13).

```
  1 MLNKIRNRKG FTLIELLIVV AIIGILAAVA IPQFTTYRIK

41 GYNSNATSDL RNLKTVLESV FADRQGYPGS
```

The pilin domain-containing protein of *Pelobacter propionicus* DSM 2379 having sequence accession number YP_901328.1 (gi:118580078) has the following sequence (SEQ ID NO:14).

```
  1 MLNKLRNRKG FTLIELLIVV AIIGILAAIA IPQFSAYRAK

41 AYNSAANSDL KNIKTGMEAF MADNQQYPGD VDYR
```

The domain from *Geobacter metallireducens* GS-15 having sequence homology to *Geobacter* pilins and having accession number YP_384358.1 (gi:78222611) has the following sequence (SEQ ID NO:15).

```
  1 MLQKLRNKKG FTLIELLIVV AIIGILAAIA IPQFAAYRQK

41 AFNSAAESDL KNTKTNLESY YSEHQFYPN
```

The pilin from *Geobacter* sp. M21 having accession number YP_003021449.1 (gi:253700260) has the following sequence (SEQ ID NO:16).

```
  1 MLNKLRSNKG FTLIELLIVV AIIGILAAIA IPQFSAYRAK

41 AYNSAANSDL KNMKTGMEAY MADRQAYPAL LDQR
```

The pilin from *Geobacter bemidjiensis* Bem having accession number YP_002139394.1 (gi:197118967) has the following sequence (SEQ ID NO:17).

```
 1 MLNKLRSNKG FTLIELLIVV AIIGILAAIA IPQFSAYREK
41 AYNAASNSDL KNFKTGLEAF NADFQTYPAA YVASTN
```

The pilin domain-containing protein from *Geobacter* sp. M18 having accession number ZP_05310612.1 (gi: 255058444) has the following sequence (SEQ ID NO:18).

```
 1 MLNKIRSNKG FTLIELLIVV AIIGILAAIA IPQFSAYRAK
41 AYNAAANSDL KNIKTGMEAY MADRQAYPVS LDER
```

In one embodiment, purified nanowire protein filaments and methods for making same are disclosed. In one embodiment, a method of purifying microbial nanowire protein filaments is provided which involves the use of detergents to solubilize any contaminating proteins. In one embodiment, the intrinsic biochemical resistance of the nanowire filaments and their aggregative nature at neutral or close to neutral pH is used to solubilize contaminating proteins with detergents, thus enabling the selective purification of the nanowires after detergent treatment.

In one embodiment, the method comprises lysis of cells expressing the nanowires, followed by selective removal of contaminating cell macromolecules, and then selective separation of pure nanowires from other proteins. See Examples 1, 2 and 5. In one embodiment, a single step purification method is used which may have yields in excess of 50%, such as up to 55% or up to 60% or higher, including any and all ranges there between. In one embodiment, the yield is at least about 63%. Higher yields, in excess of 63% may also be possible, such as up to about 95%, including any and all ranges there between. The protocol is flexible, in the sense that it can be adapted for use with substantially any sample of pili-expressing cells, substantially any method to remove contaminating cell macromolecules that do not affect the integrity of the nanowires, and substantially any method to selectively separate the nanowires from other contaminating proteins based on the nanowires' unique attributes.

The resulting nanowires are essentially pure, as they are stripped of metals, contaminating proteins, ions and other known redox cofactors such as flavins and quinones. In one embodiment, the purified nanowires are composed of a single peptide subunit (pilin or PilA) which polymerizes via hydrophobic interactions to form the pilus, i.e., nanowire filament. These nanowires can be stored dry substantially indefinitely and can be resuspended in appropriate solvents, as needed, for downstream applications. As noted above, surprisingly, these novel purified nanowires have rectifying behavior due, in part, to the absence of cellular contamination. Particular rectifying behavior is also due to the protein composition (i.e., amino acid make-up) and structure of the nanowire.

Rectifying devices using microbial nanowires are desirable because they can be mass-produced and purified from recombinant hosts that are genetically engineered to produce the nanowire subunit. The nanowire polypeptide subunits can then be assembled in vitro to form pili. This will enable the mass-production of microbial rectifiers at a low cost.

The rectifying behavior also opens, for example, the possibility to construct active devices such as transistors. With regard to nano-electronics, the rectifying behavior means that protein-based diodes (one-way conductors) can be constructed from these nanowires. In conventional microelectronics, diodes are the basic building blocks for transistors and more complex active components, including the microprocessors that run our computers. Hence, in analogy, the rectifying behavior of the nanowires opens the door to the construction of protein-based nano-electronics transistors and more complex devices.

The most basic applications in nano-electronics include, for example, radio demodulation (rectification of AM radio frequency signals to make audio signals), low voltage AC-DC power conversion, current steering, power switches and over-voltage protection. More advanced applications include, but are not limited to, the logic circuitry in electronic devices such as laptop computers, cellular phones and similar devices, further including computer chips, such as those used in the transportation industry, such as in aircraft and automobiles.

In one embodiment, the purified microbial nanowires function as one-way conductors for voltages in the range of $\pm 0.8$ V (see, e.g., Example 3).

In some embodiments, the nanowire polypeptides can be configured to include branches. Thus, the nanowire polypeptides can be assembled into a main pilus that is elongated and has a selected or desirable length. A plurality of branch pili may emanate from the main nanowire pilus at one or more substantially fixed distances along the length of the main pilus. The main pilus may also comprise one or more junctions with one or more secondary main pili, where the junctions are substantially perpendicular to the length of the main pilus.

In another embodiment, the nanowire polypeptides can be configured to form part of an apparatus. For example, the apparatus may contain at least one pilus comprising nanowires polypeptides. In other embodiments, the apparatus may contain at least one junction between pili. For example, the apparatus may include a plurality of junctions. Each junction may include a branch pilus and an elongate main pilus. For example, each junction may be situated at an interface between a branch pilus and the elongate main pilus.

As such, the inventors have also demonstrated, for the first time, that chemical modification (e.g., which may include chemical stripping) and/or genetic engineering, can be used to manipulate the protein composition, structure and binding properties of microbial nanowires to selectively modify rectification properties. Microbial rectifiers also can be manipulated via genetic engineering to bind specific ligands for sensor design, controlled and specific deposition during device manufacturing, etc.

In one embodiment, genetic engineering is used to produce nanowires with various functionalities. In one embodiment, *Geobacter sulfurreducens*, a genetically tractable member of the family Geobacteraceae, is used. See Provisional Application Ser. No. 61/378,240, filed on Aug. 30, 2010 and entitled, "Microbial Nanowires." See also U.S. application Ser. No. 13/221,495, filed on Aug. 30, 2011 and entitled, "Microbial Nanowires," which is incorporated by reference herein in its entirety.

As a result, the novel microbial rectifiers described herein can be functionalized for a variety of applications in nano-electronics and nanomedicine where rectification is used in electronic junctions, i.e., applications requiring asymmetric conductance. Such applications include, but are not limited to, diagnostic tools as well as medical interventions such as heart fibril stimulation.

The various embodiments will be further described by reference to the following examples, which are offered to further illustrate various embodiments of the present invention. It should be understood, however, that many variations and modifications may be made while remaining within the scope of the present invention.

EXAMPLE 1

Method I for Purifying Pili to Homogeneity

In this testing, it was observed that the pili of *G. sulfurreducens* did not depolymerize using mild denaturation methods, including the standard conditions with sodium dodecyl sulphate (SDS) detergent and heat treatment routinely used for denaturing SDS-electrophoresis. See Laemmli, U.K. (1970) Cleavage of structural proteins during the assembly of the head of bacteriophage T4. *Nature* 227, 680-685.

The observed biochemical resistance was due to the intrinsic resistance of the nanowire filaments to depolymerize using detergents, as well as their tendency to aggregate and form thick bundles. These thick bundles were also observed to be more resistant to depolymerization and denaturation than the individual pilus. This property suggests that the pili of *G. sulfurreducens* are very stable protein assemblies. As a result, selective separation of pili from other proteins, via preparative denaturing SDS electrophoresis, was chosen for use. (See Collinson, S. K., et al. (1991) Purification and characterization of thin, aggregative fimbriae from *Salmonella enteritidis*. *J. Bacteriol*. 173, 4773-4781).

Starting Materials

The bacterium *Geobacter sulfurreducens* strain PCA (Gsu) was originally from the American Type Culture Collection (ATCC) where it is registered under accession number ATCC® 51573™. It was obtained as a substantially pure culture and maintained under conditions known in the art in the inventors' laboratory culture collection. All chemicals, including vitamins, were from Sigma-Aldrich and had a minimum purity of 98%.

Bacterial Strains and Culture Conditions

Gsu PCA strain was used throughout the study. Cells were routinely grown at 30° C. in NB medium supplemented with 15 mM acetate and 40 mM fumarate (NBAF) before being transferred three times in a modified fresh water (FW) medium supplemented with 15 mM acetate and 40 mM fumarate (FWAF). See Coppi, M. V., et al. (2001) Development of a genetic system for *Geobacter sulfurreducens*. *Appl. Environ. Microbiol*. 67, 3180-3187 and Lovley, D. R., and Phillips, E. J. P. (1988) Novel mode of microbial energy metabolism: organic carbon oxidation coupled to dissimilatory reduction of iron or manganese. *Appl. Environ. Microbiol*. 54, 1472-1480.

A concentrated (10×) basal FW medium stock containing $NaHCO_3$ (25 g/L), $NaH_2PO_4.H_2O$ (0.6 g/L), $NH_4Cl$ (2.5 g/L), and KCl (1 g/L) was prepared. The electron donor and acceptor were prepared as sterile concentrated stocks (0.75 M sodium acetate and 1 M sodium fumarate, respectively) and the pH of the stock solutions was adjusted to 7 prior to autoclaving.

Vitamins were prepared as separate solutions as described in Balch, W. E., et al. (1979) Methanogens: reevaluation of a unique biological group. *Microbiol. Rev*. 43, 260-296. Trace minerals were prepared as described in Lovley, D. R., et al. (1984) Rapidly growing rumen methanogenic organism that synthesizes coenzyme M and has a high affinity for formate. *Appl. Environ. Microbiol*. 48, 81-87, except that $ZnSO_4$ was replaced with $ZnCl_2$ (0.13 g/L), and $Na_2WO_4.2H_2O$ (0.025 g/L) was added. FWAF medium contained FW stock (96 ml/L), 0.75 M sodium acetate (20 ml/L), 1 M sodium fumarate (40 ml/L), vitamin solution (10 ml/L), mineral solution (10 ml/L) and $ddH_2O$ to a final volume of 1 L. The medium was dispensed in pressure tubes or serum bottles, sparged with $N_2:CO_2$ (80:20) to remove dissolved oxygen and sealed with butyl rubber stoppers and aluminum tear off seals (Wheaton) prior to autoclaving. For pili induction, exponentially-growing cells from FWAF cultures grown at 30° C. were subcultured in 100 ml of fresh FWAF with 30 mM acetate and 40 mM fumarate and incubated at 25° C. until they reached early stationary phase (ca. 72 h). (See, Reguera, G., et al. (2005) Extracellular electron transfer via microbial nanowires. *Nature* 435, 1098-1101).

Isolation and Purification of Pili

Pili were purified to homogeneity using a modified protocol described in Collinson, S. K., et al. (1991) Purification and characterization of thin, aggregative fimbriae from *Salmonella enteritidis*. *J. Bacteriol*. 173, 4773-4781. Pili-expressing cells were harvested by centrifugation (13,000×g) for 15 min at 25° C. and resuspended in 6 ml of 10 mM Tris HCl, pH 8.0 (Tris buffer; Invitrogen, 99.9%). The cells were lysed by sonication (5 1-min at 4° C. per 1 ml of cell suspension; Branson Sonifier 450) before adding RNase A (bovine pancreas; Roche Diagnostics) and DNase I (bovine pancreas, Sigma, 91% purity) enzymes to a 0.1 mg/ml final concentration and $MgCl_2$ (J. T. Baker, 99.4%) to a final concentration of 1 mM. The cell extracts were incubated at 37° C. for 20 min to enzymatically degrade the nucleic acids in the sample. Lysozyme (hen egg white, Roche Diagnostics) was then added to a concentration of 1 mg/ml and incubated at 37° C. for 40 min with gentle shaking (200 rpm, Innova 4340, New Brunswick). Cell membranes and proteins in the extract were solubilized with sodium dodecyl sulfate (SDS, 1% final concentration; Sigma 98.5%) after incubation at 37° C. for 30 min. The SDS-insoluble fraction was collected by centrifugation (12,100×g, 15 min, 25° C.) and washed twice with 6 ml of Tris buffer. The SDS-insoluble fraction in Tris buffer was digested again with RNase, DNase and lysozyme, as described above. Mechanical vortexing (Fisher Scientific) was used to mix the samples.

Samples with large clumps and/or aggregates were subjected to 2 additional cycles of sonication for 1 min at 4° C. The insoluble fraction was collected as described above, washed twice, and resuspended in 1 ml of Tris buffer. When needed, the sample was stored at −20° C. overnight. The protein sample was suspended in 2 ml of SDS-polyacrylamide gel electrophoresis (PAGE) sample buffer (10% [v/v] glycerol; 5% [v/v] b-mercaptoethanol; 2% [w/v] SDS, and 62.5 mM Tris HCl, pH 6.8) and boiled for 15 min. The SDS-treated sample was loaded on top of a preparative 12% polyacrylamide gel with a 5% stacking gel, and subjected to electrophoresis at 40 mA for 5 h using Prep Cell 491 (Bio-Rad). The material that did not enter the stacking gel was recovered by aspiration with a pipette and washed three times with 1 ml $ddH_2O$ of double distilled water by centrifugation (12,100×g, 15 min, 25° C.).

The protein in the SDS-insoluble fraction was extracted twice with 95% ethanol (Decon Laboratories) and lyophilized or dried in a Speed Vac system (Savant Instruments Inc) at room temperature for approximately 20 min. This ethanol step also solubilized organic contaminants such as quinone-like compounds or organic cofactors. The dried protein was resuspended in 1 ml of $ddH_2O$ and vortexed for 60 seconds to break up the large clumps. Poorly-bound protein in the insoluble material was extracted with 0.2 M glycine (pH 1.5, adjusted with HCl; Invitrogen) at 100° C. for 10 min. The insoluble fraction was recovered by centrifugation (16,000× g, 25 min, 4° C.), washed five times with $ddH_2O$, and lyophilized or dried in a SpeedVac at room temperature until completely dry. The dried sample was then stored at −20° C. for short-term use or flash frozen in liquid nitrogen for long-term use.

Quantitative elemental analysis of the purified pili preparations was performed by Inductively Coupled Plasma-Atomic Emission Spectrometry (ICP-AES) using a Thermo Jarrell-Ash Enviro 36 Inductively Coupled Argon Plasm (Chemical Analysis Laboratory, University of Georgia, Athens). For these experiments, 1 ml aqueous samples of purified pili containing 40-70 micrograms of protein per milliliter were analyzed in reference to blank control samples (without protein). When indicated, ethylenediaminetetraacetic acid (EDTA, Invitrogen) was added to the sample at a final concentration of 0.1 mM prior to the ICP-AES analyses. Protein concentration was determined using the bichinchoninic acid (BCA) assay as described in Smith, P. K., et al. (1985) Measurement of protein using bicinchoninic acid. *Anal. Biochem.* 150, 76-85 (Pierce®, Thermo Scientific) with Bovine Serum Albumin (BSA) as the protein standard.

Protein Electrophoresis

Dried pili preparations were resuspended in 15 ml of $ddH_2O$ containing 2% (w/v) Octyl-β-D-Glucopyranoside (OG) (Sigma, 98%) and incubated at room temperature for 1 h prior to SDS-PAGE. SDS-PAGE was performed according to the method described in Laemmli, U.K. (1970) Cleavage of structural proteins during the assembly of the head of bacteriophage T4. *Nature* 227, 680-685 as modified by the method described in Ames, G. F. (1974) Resolution of bacterial proteins by polyacrylamide gel electrophoresis on slabs. *J. Biol. Chem.* 249, 634-644. The OG-treated sample was boiled in SDS-PAGE sample buffer prepared according to the procedure discussed in Laemmli, U.K. (1970) Cleavage of structural proteins during the assembly of the head of bacteriophage T4. *Nature* 227, 680-685 and subjected to electrophoresis on 12% ReadyGels (Bio-rad) using a Mini Protean Tetra Cell apparatus (Bio-Rad). After electrophoresis, the gels were silver stained using the Pierce® Silver Stain for Mass Spectrometry kit (Thermo Scientific), following the instructions supplied by manufacturer.

After silver-staining, the ca. 7-kDa PilA protein band was excised from the gel, destained and digested with trypsin following the procedure described by manufacturer (Pierce® Silver Stain for Mass Spectrometry, Thermo Scientific). The peptides in the tryptic digest were concentrated and purified chromatographically with $C_{18}$ reversed-phase media (Zip-Tip®, Millipore) and separated by matrix assisted laser desorption ionization-time of flight spectrometry (MALDI-TOF, Shimadzu Axima). Peptide identification and prediction of potential contributions of post-translational modifications to the peptide mass was performed using the MS-DIGEST tool at the ProteinProspector database from the University of California, San Francisco, http://prospector.ucsf.edu/prospector/cgi-bin/msform.cgi?form=msdigest.

Western Blot (Immunoblot) Analysis

Proteins separated by SDS-PAGE were electrophoretically transferred to a nitrocellulose membrane (HyBond ECL™, Amersham GE Healthcare) at 50 V for 15 min using a Mini Protean Tetra Cell apparatus (Bio-rad). The rapid western blotting kit (Amresco®) was used for the electrophoretic transfer and membrane blocking, following manufacturer's recommendations. After blocking, the membrane was incubated in 10 ml rapid antibody diluent solution (45 min, room temperature, gentle agitation) with a 1:5,000 dilution of the primary antibody (rabbit α-PilA polyclonal antibodies raised against the 42 amino acids at the carboxy-terminus of the PilA protein) and a 1:2,500 dilution of goat α-PilA rabbit IgG antibodies conjugated to the $Cy^{tm}$ 5 fluorescence dye (ECL™ Plex, Amersham GE Healthcare). The membrane was washed in rapid wash solution provided by manufacturer (3 times 5 min). The membrane was then scanned with Typhoon imager operated in fluorescence mode (excitation at 633 nm, 670 BP 30 filter, and PMT setting at 600 V) to visualize the protein bands that hybridized with the primary antibodies.

Microscopy

Confocal Laser Scanning Microscopy (CLSM)

For Confocal Laser Scanning Microscopy (CLSM), dried preparations of purified pili were dissolved in phosphate buffer saline (PBS), deposited on the surface of a glass coverslip and allowed to adsorb for 30 min. The adsorbed pili were then washed with PBS and fixed with 100 microliters of 3.7% paraformaldehyde in PBS. After washing with PBS, the samples were incubated for 30 min in PBS containing 1% BSA, before adding the anti-PilA primary antibody (1:100) and incubating at 4° C. overnight. Following three washes in PBS-1% BSA, the samples were incubated with the secondary antibody (α-PilA rabbit conjugated to Alexa fluor 488 dye, 1:1000) for 1 h. The coverslip was then washed three times with PBS buffer and examined with Zeiss LSM Pascal confocal microscope equipped with a Plan-Neofluar 63× oil objective (excitation, 488 nm; emission, 505-535 nm).

Transmission Electron Microscopy (TEM)

For transmission electron microscopy (TEM), an aqueous solution of purified pili was adsorbed on a carbon-copper grid (Mesh 300, Electron Microscopy Sciences), negatively stained with 1% (w/v) uranyl acetate in distilled water. The negatively stained samples were examined with a Jeol 100 CX electron microscope (Japan Electron Optic Laboratory) operated at 100 kV.

Scanning Probe Microscopy

Distal (lateral) and axial (length) conductivity measurements were performed, respectively, by scanning tunneling microscopy (STM) and conductive probe-atomic force microscopy (CP-AFM). STM imaging and spectroscopy was performed as described in Veazey, J. P., et al. (to be published in 2011) Electronic structure of *Geobacter sulfurreducens* pilus nanowires probed by Scanning Tunneling Microscopy. *Phys. Rev. B.* For CP-AFM measurements a Bio-AFM-CF instrument (Asylum) was used and a gold electrode grid nanofabricated onto a silicon substrate was used for biological deposition. For the fabrication of the gold grid, photoresist (Shipley S1813) was spin-coated onto silicon wafers having a 300 nm thermal oxide layer ($SiO_2$). After photoresist development, patterned gold electrodes were deposited by thermally evaporating 5 nm of titanium followed by 25 nm of gold onto the surface of the wafer. A solution containing ca. 40-70 micrograms of purified pili protein per milliliter in $ddH_2O$ were then deposited onto the electrodes, left to adsorb for 25 minutes, and then wicked dry with absorbent paper. CP-AFM was performed with Pt-coated cantilevers having spring constant 2 N/m (Veeco). Pilus nanowires lying across the gold-$SiO_2$ interface were first identified in imaging mode. For Current (I) vs voltage (V) ("I-V") measurements, the tip was placed on a point of the pilus lying on the $SiO_2$. Positive controls were generated by positioning the tip on the gold electrode, while negative controls were produced by positioning the tip on the $SiO_2$ substrate at 100-nm distances from the gold edge.

Results

Figure 2B:
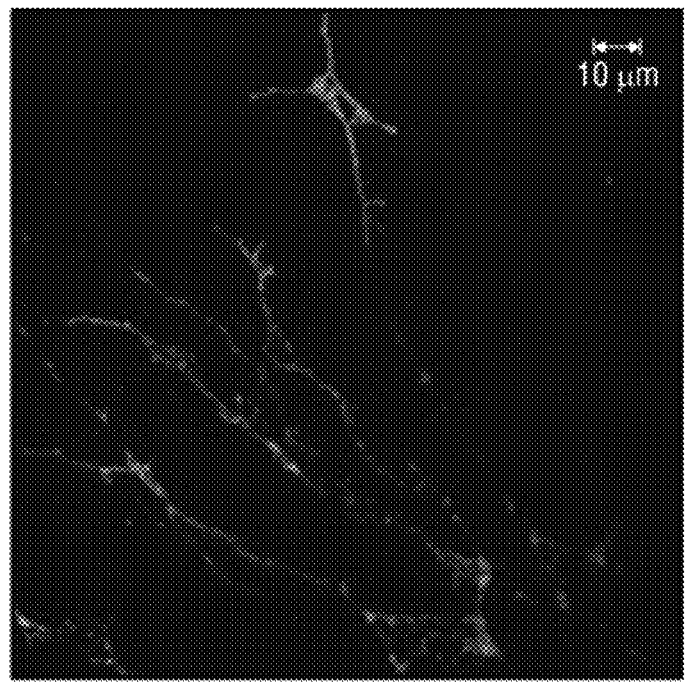
FIG. 2B is a Confocal Laser Scanning Microscopy (CLSM) micrograph of anti-PilA immunodetected purified pili of *G. sulfurreducens* according to an embodiment.
Figure 2C:
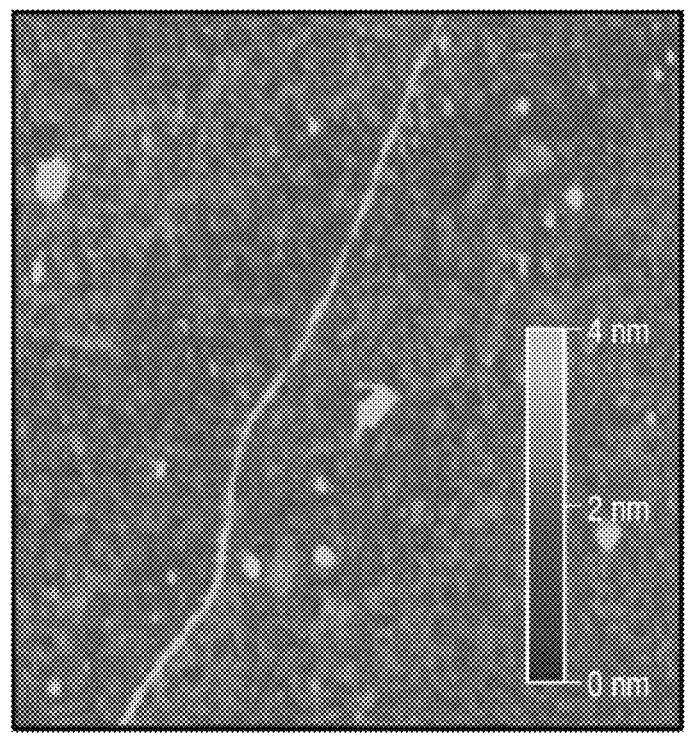
FIG. 2C shows AFM imaging of a pilus filament in a 2 μm by 2 μm field according to an embodiment.

Transmission electron microscopy (TEM) of negatively-stained SDS-insoluble samples (FIG. 2A) confirmed the presence of bundles of fibrils morphologically similar to the pili displayed on the surface of cells of *G. sulfurreducens*. Furthermore, the fibrils were free of obvious cellular debris. The presence of the PilA subunit in the purified fibrils was detected immunologically by confocal laser scanning microscopy (CLSM) of purified fibrils hybridized to polyclonal antibodies raised against a recombinant truncated form of the PilA pilin subunit (anti-PilA) and fluorescently-labeled secondary antibodies (FIG. 2B). Atomic Force Microscopy (AFM) was used to image the purified pili from *G. sulfurreducens* deposited on a HOPG substrate and measure the average width of the fibrils, which was in the 4-5 nm range. FIG. 2C shows the resulting AFM image of the pilus fiber with the inset showing the height color scale in nm.

Denaturing SDS-PAGE and immunodetection by Western blot using polyclonal anti-PilA antibodies was used to investigate the protein composition of the pili and assess its purity. Standard denaturation conditions with SDS detergent and heat treatment did not fully depolymerize the pili into the pilin subunit. However, treatment with octyl-glucoside partially depolymerized the pili into oligomers of various sizes and a protein band that migrated as between 3 and 10 kpa in the gel, consistent with the predicted size of the mature PilA protein (6.5 kpa without any post-translational modifications). See FIG. 3A, which shows denaturing SDS-PAGE electrophoresis in a 4-20% polyacrylamide gel showing pili oligomers in untreated controls (lane 2) and pilus oligomers of various sizes and the ca. 7 kpa PilA band in samples pretreated with 1% (lane 3) or 2% (lane 4) octyl-glucoside are shown in FIG. 3A. Lane 1 shows molecular weight markers, with the numbers at left showing molecular weights of the markers in lane 1.

The band was positively detected as PilA in immunoblots with anti-PilA antibodies Anti-PilA immunoblot of 2% OG-treated purified (lane 2) pili following SDS-PAGE in 12% polyacrylamide gels showing the PilA band migrating between the 3 and 10 kDa molecular weights markers (lane 1) are shown in FIG. 3B. Numbers at left are the molecular weights of the markers shown in lane 1.

The low-migrating PilA band also was excised from the silver-stained gel shown in FIG. 3A, destained, and proteolytically digested with trypsin. As FIG. 4 and Table 1 show, the 7-kDa protein band that was electrophoretically separated after depolymerizing purified pili with 2% octyl-glucoside was extracted from the gel, digested with tryptin and the mass of the tryptic peptides was analyzed by MALDI-TOF. Peptide mass fingerprinting of the tryptic digest by MALDI-TOF identified several PilA peptides, some carrying potential post-translational modifications, such as the N-methylation of the phenylalanine at the peptides amino-terminus that all pilins have. Details of peak assignment are presented in Table 1. This confirmed the identity of the PilA band. Taken together, these results demonstrated that the pili of *G. sulfurreducens* were selectively purified to homogeneity.

TABLE 1

Masses of Tryptic Peptides of PilA from *Geobacter sulfurreducens* Detected with MALDI-TOF Mass Spectrometry

| Peak | Expected mass | Observed mass | Sequence[a] | SEQ ID NO: | Modification |
|---|---|---|---|---|---|
| 1 | 2205 | 2207 | (K)TALESAFADDQTYPPES | 2 | 2 pospho, acetyl |
| 2 | 2220 | 2221.6 | (K)TALESAFADDQTYPPES | 3 | 2 phospho, acetyl, methyl |
| 3 | 2280 | 2280.4 | (R)NLKTALESAFADDQTYPPES | 4 | methyl |
| 4 | 2295 | 2294.9 | (R)NLKTALESAFADDQTYPPES | 5 | 2 methyl |
| 5 | 2309 | 2308.5 | (R)NLKTALESAFADDQTYPPES | 6 | acetyl |
| 6 | 3326 | 3323.9 | FTLIELLIVVAIIGILAAIAIPQFSAYRVKA(V) | 7 | — |
| 7 | 3341 | 3337.6 | FTLIELLIVVAIIGILAAIAIPQFSAYRVKA(V) | 8 | methyl |
| 8 | 3356 | 3353.6 | FTLIELLIVVAIIGILAAIAIPQFSAYRVKA(V) | 9 | 2 methyl |

[a]Amino acids in parenthesis are trypsin cleavage position

The lack of proteins, other than PilA-containing oligomers, in the pili fractions excluded the possibility of c-cytochromes being associated with the pili. However, it did not exclude the possibility of metals being directly bound to the pilus shaft. Amino acid residues can be positioned in the folded protein to form structural motifs for metal coordination. Bound metals not only enable electron transfer reactions but also stabilize the protein's secondary structure. The SeqCHED server described in Levy, R., et al. (2009) Prediction of 3D metal binding sites from translated gene sequences based on remote-homology templates. *Proteins* 76, 365-374 was used within the SPACE tools suite described in Sobolev, V., et al. (2005) SPACE: a suite of tools for protein structure prediction and analysis based on complementarity and environment. *Nucleic Acids Res.* 33, W39-43 to identify soft (Zn, Fe, Ni, Cu, Co, Mn) and promiscuous, hard (Mg, Ca) metal-ion binding sites in the mature PilA amino acid sequence. However, none were identified. Despite the lack of conserved metal-binding sites in the pilin, the assembly of pilin subunits to form the pilus shaft could create structural and sequence motifs for metal coordination. To investigate this, Inductively Coupled Plasma-Atomic Emission Spectroscopy (ICP-AES) was used for elemental analysis of aqueous samples of the purified pili in reference to protein-free 'blank' controls. This technique has been traditionally used for metal analyses of metalloproteins because of its high specificity and sensitivity at the identification and quantification of trace elements based on the distinct energy that excited electrons emit at a given wavelength as they return to ground state (See Ma, R., et al. (2004) Speciation of protein-bound trace elements by gel electrophoresis and atomic spectrometry. *Electrophoresis* 25, 2469-2477. No significant differences were observed between samples and protein-free controls for most of the elements analyzed. These results are shown in Table 2 below:

TABLE 2

Elemental analyses by ICP-AES to purified pili in the absence or presence of EDTA

| Metal | Lower LOD (ppm)[a] | Lower LOD ($10^{16}$ atoms)[b] | Elements ($10^{16}$ atoms)[c] | Elements/EDTA ($10^{16}$ atoms)[d] |
|---|---|---|---|---|
| Al | 0.06 | 0.13 | 0.464 ± 0.349 | <LOD |
| Sb | 0.09 | 0.05 | | |
| As | 0.08 | 0.06 | | |
| Ba | 0.06 | 0.03 | <LOD | <LOD |
| Be | 0.09 | 0.60 | | |
| B | 0.10 | 0.56 | <LOD | <LOD |
| Cd | 0.06 | 0.03 | <LOD | <LOD |
| Ca | 0.05 | 0.08 | 0.222 ± 0.192 | <LOD |
| Cr | 0.06 | 0.07 | <LOD | <LOD |
| Co | 0.06 | 0.06 | <LOD | <LOD |
| Cu | 0.07 | 0.07 | <LOD | |
| Fe | 0.05 | 0.05 | 0.118 ± 0.1 | <LOD |
| Pb | 0.06 | 0.02 | <LOD | <LOD |
| Mg | 0.03 | 0.07 | 0.134 ± 0.116 | <LOD |
| Mn | 0.10 | 0.11 | <LOD | <LOD |
| Mo | 0.05 | 0.03 | <LOD | <LOD |
| Ni | 0.10 | 0.10 | <LOD | <LOD |
| P | 0.09 | 0.18 | 4.499 ± 3.906 | <LOD |
| K | 0.50 | 0.77 | 3.671 ± 3.120 | <LOD |
| Se | 0.09 | 0.07 | | |
| Si | 0.50 | 1.07 | <LOD | <LOD |
| Ag | 0.10 | 0.06 | | |
| Na | 0.50 | 1.31 | 38.337 ± 33.232 | 6.867 |
| Sr | 0.05 | 0.03 | <LOD | <LOD |
| Tl | 0.05 | 0.01 | | |
| Ti | 0.10 | 0.13 | | |
| V | 0.15 | 0.18 | | |
| Zn | 0.05 | 0.05 | <LOD | <LOD |

[a]Instrumental Limits of Detection (LOD)
[b]Calculated for total volume of 1 ml.
[c]Elements detected in purified pili preparations (<LOD, lower than lowest detection limits)
[d]Elements detected in purified pili preparations after EDTA treatment (<LOD, lower than lowest detection limits)

The pili were also treated with low (0.1 mM) concentrations of EDTA to remove weakly bound elements carried over during the course of purification. Among the metal ion cofactors known to catalyze electron transfer (Fe, Cu, Mo) or redox (Fe, Cu, Mn, Co and Ni) reactions, only Fe was detected (0.19±0.14 atoms per pilin). However, as Table 2 shows, Fe levels varied widely from sample to sample, suggesting it was a trace contaminant and mild treatment with EDTA effectively removed it from the pili samples.

Quinones such as ubiquinones and menaquinones are lipid soluble molecules that function as the primary electron carriers of the bacterial inner membrane and serve as electronic link to membrane-bound respiratory complexes, a process that requires quinones to bind to specific structural motifs in quinone-reactive redox proteins. Because of their hydrophobic nature, quinones bind motifs located in hydrophobic regions of redox proteins. Type IV pili are predicted to have a narrow (6-11 Å) hydrophobic central channel. Because the pilus is anchored on the inner membrane of Gram-negative bacteria, its inner hydrophobic channel could potentially house quinones and create an internal pathway for electron transfer free of solvents.

Figure 5:
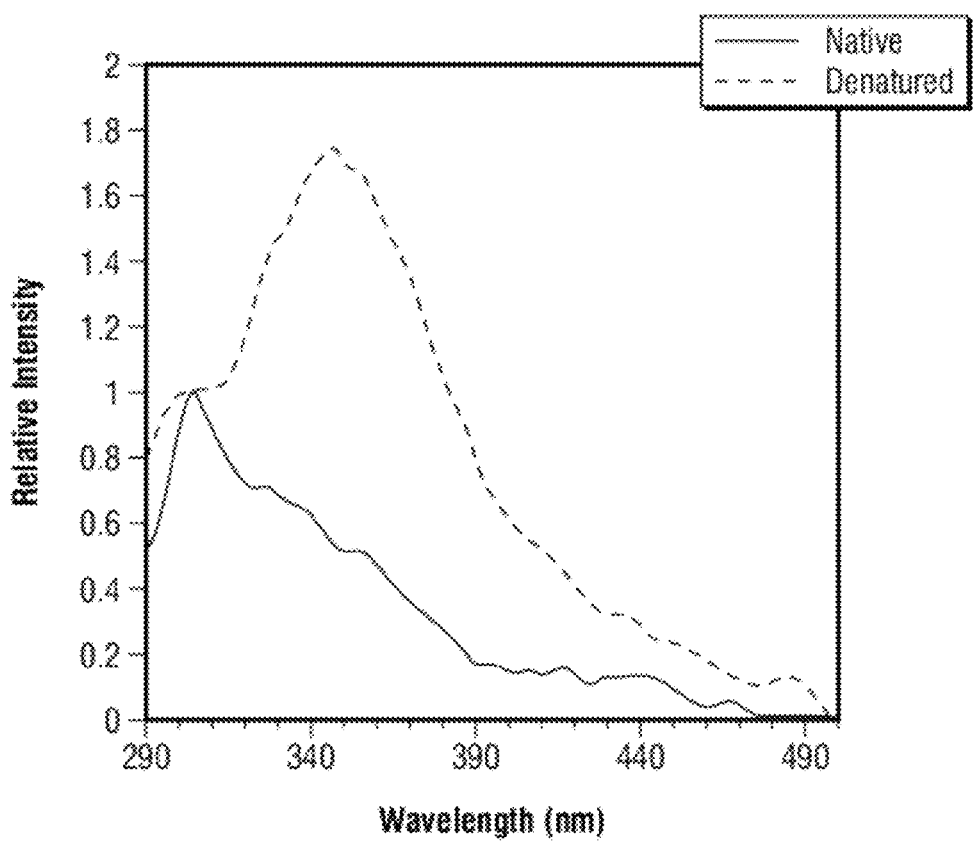
FIG. 5 is a fluorescence spectroscopy graph of purified nanowires showing no emission peak in the 400-500 nm emission range, which is the range of all known quinones according to an embodiment.

As FIG. 5 shows, fluorescence spectroscopy of the purified nanowires revealed no emission peak in the 400-500 nm emission ranges of all known quinones (See Cory and McKnight. Fluorescence Spectroscopy Reveals Ubiquitous Presence of Oxidized and Reduced Quinones in Dissolved Organic Matter. Environ. Sci. Technol. 2005, 39, 8142-8149). An emission peak at a 305 nm wavelength was detected, however, which corresponds with nanowire tyrosine residues. Additionally, the nanowire structure was opened up using partial denaturation of the nanowire with 8M urea for two (2) hrs at room temperature. No internal quinones were exposed as a result. Denatured samples showed the tyrosine peak at above 300 nm and a large peak close to 350 nm, which is consistent with loss of tyrosine fluorescence quenching as the protein structure is denatured.

The results presented thus far demonstrated the proteinaceous composition of the purified pili, ruling out its association to redox-active cofactors, organic or inorganic.

Figures 6A, 6B:
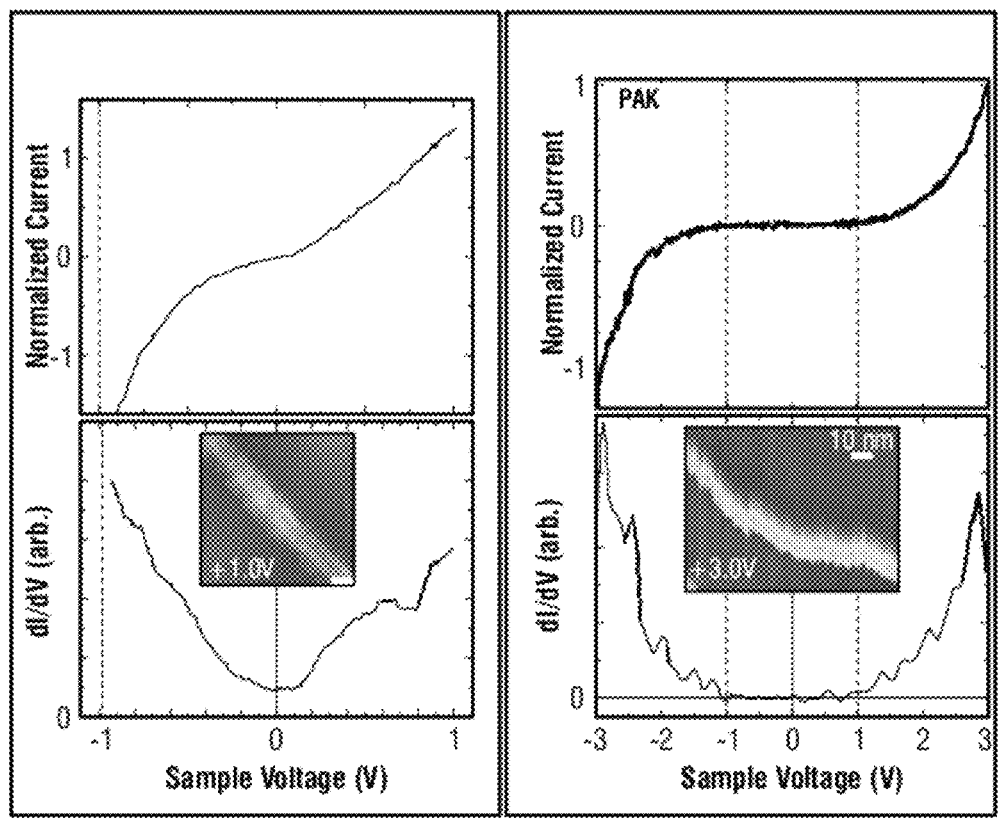
FIGS. 6A and 6B show distal conductivity measurements of the purified pili by STM according to an embodiment.

The purified pili were then used to investigate the contribution of the pilus protein matrix to extracellular electron transfer in *G. sulfurreducens*. Scanning tunneling microscopy (STM) was used to probe the axial (lateral) conductivity of purified pili (See FIGS. 6A and 6B). STM provides a higher spatial resolution probe and permits more direct electronic characterization compared to the CP-AFM approach used in earlier work to demonstrate the conductive nature of mechanically-sheared pili preparations. No chemical fixation was used to prevent potential artifacts. Applying a voltage causes electrons to tunnel from occupied states at the sample surface into unoccupied states of the tip, or vice versa. As the amount of tunneling current is proportional to the number of available electronic states, STM can probe the local density of states of the pili and measure the contribution of individual amino acids in the protein matrix. The method has been successfully applied to study the surface topography and electronic properties of biological samples. STM imaging of purified pili showed periodic conducting filaments of the expected diameter (FIGS. 6A and 6B). The bright spots observed in the pilus are not taller in the topographical sense, but represent regions of the pilus that supply more tunneling current due to an increase in the local density of states. These bright locations are probably due to molecular sub-structures, consistent with the presence of conductivity 'hot spots' such as redox-active amino acids. Current (I) vs voltage (V) measurements taken at various locations of the pilus confirmed the metallic (ohmic) behavior at biological (±1 V) voltages (FIGS. 6A and 6B).

Controls with non-conductive purified pili from *Pseudomonas aeruginosa* strain K (PAK) were used to demonstrate the insulating behavior of other pili at biologically-relevant voltages. Large sample voltages, greater than 2 V, were necessary to image the PAK pili. At these voltages, tip instabilities often result due to the large electric field between the tip and the sample, which causes distortions and noise in the imaged data (FIGS. 6A and 6B). This is even more pronounced for the pilus nanowires, due to the high tunneling rates produced by such highly conductive materials at high-voltages. The PAK pili thus serve as insulating controls in the ±1 V range, which represent biologically relevant voltages (often in the mV range). The PAK's distal conductivity at high voltages possibly reflects electron transfer through the peptide backbone. These results demonstrate that the protein casing of the pilus nanowires can conduct electrons laterally at ±1 V voltage ranges. In contrast, structurally similar protein filaments, such as the PAK pili, cannot. These results suggest that specific amino acids in the pilus nanowires function as electronic conduits to promote electron transfer reactions.

The STM studies presented above probed the distal conductivity of the pilus, thereby demonstrating that the protein matrix conducted electrons at distances in the same ranges as the pilus diameter (4-5 nm). In order to establish the upper range that the pilus protein matrix can conduct electrons, we used CP-AFM to probe the axial (length) conductivity of pili deposited onto nanofabricated gold grids lying on an insulating silicon substrate. We used the conductive AFM tip to probe the conductivity of the pilus on the gold electrode (equivalent to the distal measurement) and compared these measurements to the current measured when the tip was positioned at various points on the pilus filament lying on the insulating silicon substrate.

Figure 7:
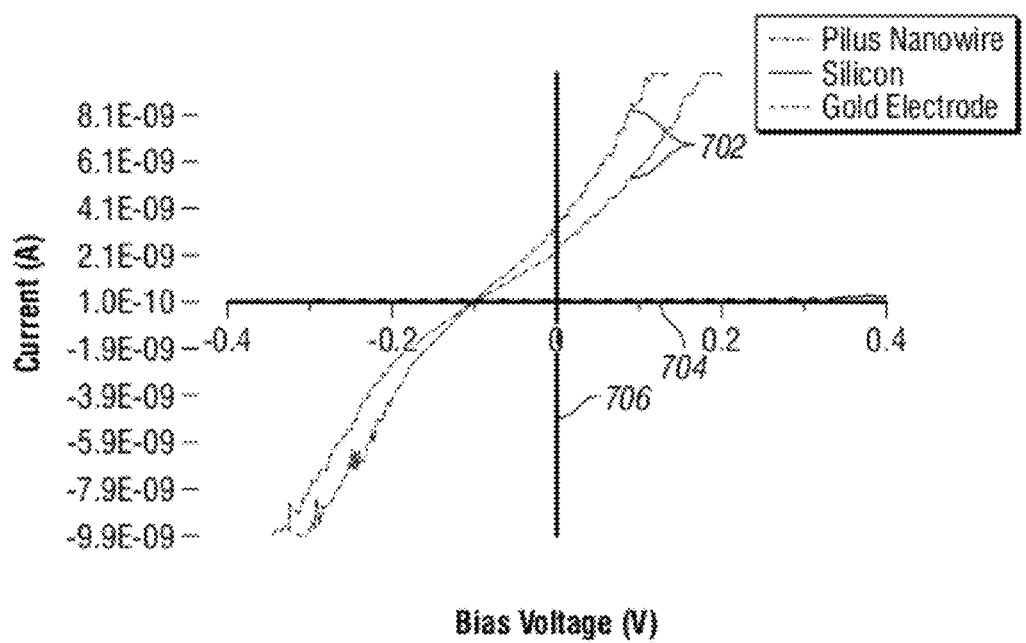
FIG. 7 shows axial conductivity along the purified pilus nanowires by Conductive Probe-Atomic Force Microscopy (CP-AFM) according to an embodiment.

See, for example, FIG. 7, which shows raw (non-normalized) data which demonstrate that *Geobacter* pili can transfer electrons along their length. Curve 702 shows the current versus voltage with the AFM tip touching the purified pilus. As curve 702 shows, there is electrical conductivity along the axial length of the nanowire. The same pilus touches a gold surface electrode 200 nm away from the AFM tip. Therefore, the measurement shows the current passing from the tip, through the nanowire, and to the gold electrode. Curve 704 indicates that the AFM tip was touching the Si substrate 100 nm away from the gold edge and was not touching a nanowire. No measurable current results were observed.

For the positive control 706, the AFM tip was directly positioned on the gold electrode. As FIG. 7 shows, the conductivity of the direct tip-to-gold pathway was large, as expected.

The I-V curves clearly demonstrate, for the first time, the conducting behavior of the pilus with respect to axial conductivity, consistent with known conducting behavior in distal measurements by CP-AFM, as described in Reguera et al. 2005. Nature 435:1098-101. Moreover, this behavior is consistent with similar mechanisms of the protein matrix mediating both distal and axial charge transport in the pili.

These results demonstrate that the protein matrix of the pili of *G. sulfurreducens* can, by itself, catalyze electron transfer reactions at distances that greatly exceed the known limits for protein-based electron transfer.

Furthermore, these results rule out any contribution from organic and inorganic cofactors known to mediate long-range electron transfer in proteins and support, instead, a mechanism exclusively mediated by the protein matrix. A solvent-free pathway through the pilus central channel mediated by quinones is not plausible because external organic molecules were extracted with ethanol from the conductive pili during purification and no emission peaks were detected by fluorescence spectroscopy to purified nanowires or partially denatured nanowires. The hydrophobic nature of the inner pilus channel also prevents solvents from filling the pilus internal cavity, which is necessary for a mechanism of electron transfer through an inner electrolytic channel. In support of this, elemental analyses by ICP-AES detected only trace amounts of the alkali metal sodium after removing weakly bound ions with EDTA.

The measured concentrations varied from sample to sample without affecting the conductivity measurements of the pili preparations, suggesting they do not provide sufficient ionic strength to contribute to the pilus conductance. The pilus nanowires also lacked associated metals that are biologically relevant. From all the inorganic elements known to participate in electron transfer and redox catalysis in biological systems, only some low levels of iron were detected in samples that were not treated with EDTA. Again, there was a lot of variability from sample to sample, with samples lacking any detectable levels of Fe, yet producing consistent I-V curves by STM and CP-AFM. Samples with the highest levels of Fe had the equivalent of one atom of iron per 5 pilin subunits assembled along the pilus shaft.

With an estimated assembly of 3.6 pilin subunits per turn and a pilus pitch of 37 Å, the distance between potential iron redox centers in the pilus would exceed 51 Å. This is close to 5 times the optimum distance (<14 Å) established for electron transfer between metal-containing redox centers. Other metals such as boron or cadmium, which are commonly used to metalize insulating materials during the manufacturing of inorganic nanowires were also below the limits of detection. Electron transfer over distances beyond the 25 Å theoretical and experimental tunneling limits supports the involvement of multistep tunneling (hopping), single-step superexchange tunneling pathways and/or yet to be discovered transport mechanisms mediated by the protein matrix. See also Table 3 below:

TABLE 3

Atoms per pilin detected by ICP-AES analysis of pili samples

| | atoms/pilin | Stdev [a] |
|---|---|---|
| Al | 0.801 | 0.252 |
| Ca | 0.348 | 0.301 |
| Fe | 0.189 | 0.140 |
| K | 5.835 | 4.561 |
| Mg | 0.209 | 0.182 |
| Na | 60.080 | 52.080 |
| P | 7.050 | 6.121 |

[a] Standard deviation of three replicates

In this testing it was demonstrated that purified pili are assemblies of a single peptide subunit, the PilA pilin, and lack associated proteins or metals. Transport measurements demonstrated that the pilus protein matrix conducted electrons distally across the 4-5 nm-thick pilus shaft and axially at hundreds of nm distances. These distances greatly exceed the theoretical and experimental maximum limits of ca. 25 Å reported for single-step electron tunneling reactions through protein matrices and make the pilus nanowires a new paradigm in protein electron transfer.

EXAMPLE 2

Molecular Rectifying Behavior of the Pilus Nanowires of *Geobacter*

Unless otherwise stated, materials and methods were as described in Example 1. Prior to analyses the dry purified pili were resuspended in ddH$_2$O with 1 mM EDTA to remove trace elements.

Figure 8:
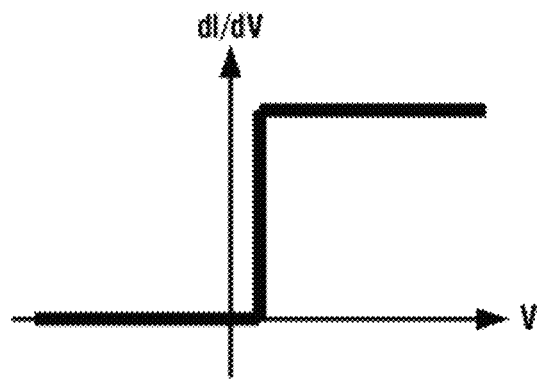
FIG. 8 shows a schematic density-of-states curve for an ideal rectifier.

The molecular rectifying behavior of purified microbial nanowire was demonstrated using a STM. By probing the nanowire with a sharp tip, this electronic information can be resolved atom-by-atom. In addition to atomic scale images of the material, STM can monitor the tunneling current at a particular location as a function of the applied voltage. This information is directly related to the electronic density of states. A material with a high density of states acts as an electronic conductor. Likewise, a material with a low density of states acts like an insulator. In contrast, a rectifier, or diode, is an electronic component that acts as either a conductor or an insulator, depending on the sign of the voltage. The resulting action is that current can only flow in one direction. FIG. 8 illustrates the density of states for an ideal rectifier.

This example provides reproducible measurements showing rectifying behavior on the edges of microbial nanowires. In this example, cells of the bacterium *Geobacter sulfurreducens* were grown under nanowire-inducing conditions (incubation at 25° C.) and the nanowires were purified as described in Example 1 and resuspended in ddH$_2$O with 1 mM EDTA. The purified nanowires were composed of a single peptide subunit that polymerizes via hydrophobic interactions to make the nanowire filament. The nanowires were adsorbed and air-dried onto a graphite surface prior to STM analyses. The STM tip was positioned on the nanowire to acquire electronic information.

Figure 9:
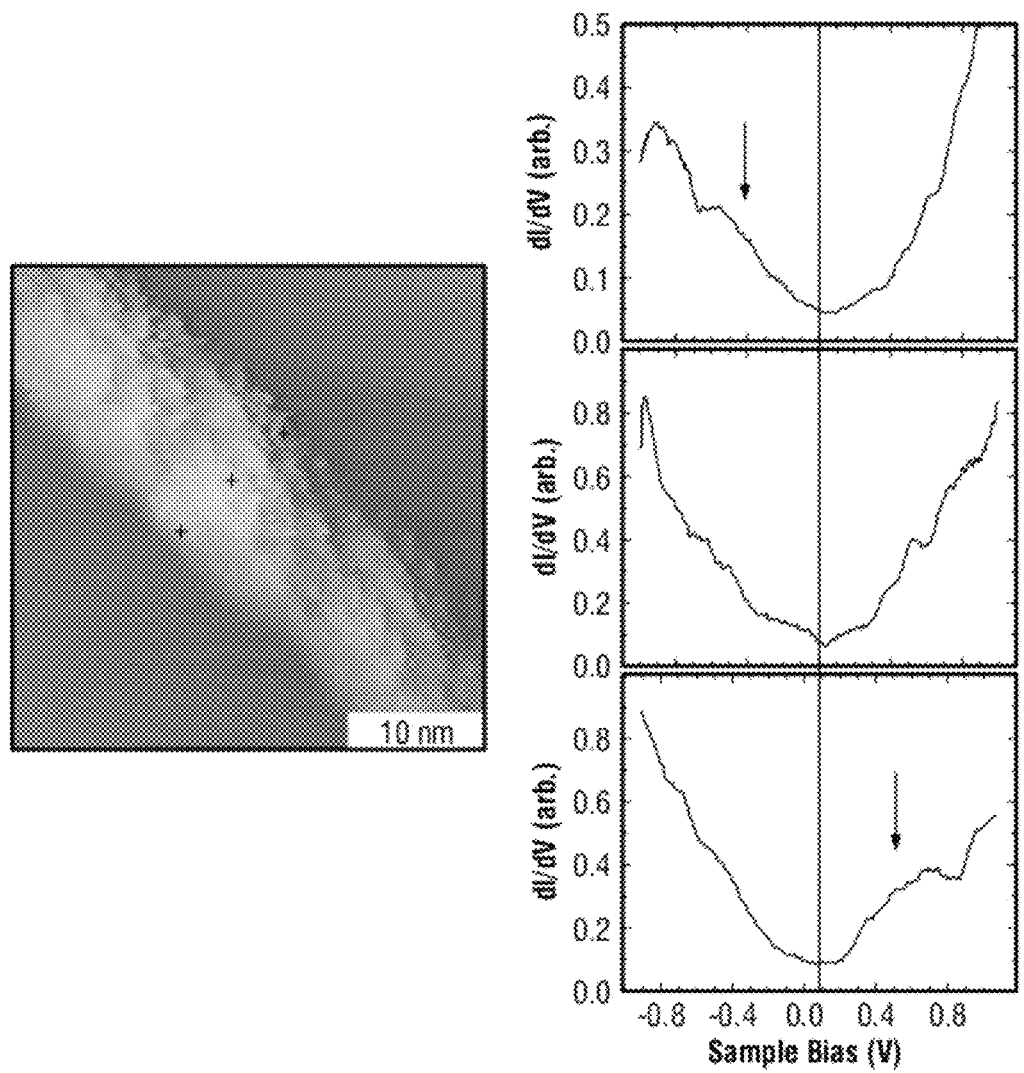
FIG. 9 is a STM topographical image (left) of a purified nanowire deposited onto a graphite surface together with three spectroscopic measurements of the electronic density of states (right) according to various embodiments.

FIG. 9 includes a STM topographical image (left) of a purified nanowire deposited onto a graphite surface together with three spectroscopic measurements of the electronic density of states (right). The top and bottom curves on the right panel were acquired at the top edge and bottom edge, respectively, at the locations indicated by the "+" symbols on the left image. The middle curve was acquired at the central "+" symbol. The blue arrows indicate enhanced density of states. The key features are highlighted by the arrows, which indicate enhanced density of states near ±0.4 V. As the enhancement depends on the sign of the voltage (i.e., the curves are asymmetric with respect to the horizontal axis), the overall behavior at low voltages, in the range of ±0.8 V, is consistent with a rectifier.

Figure 10:
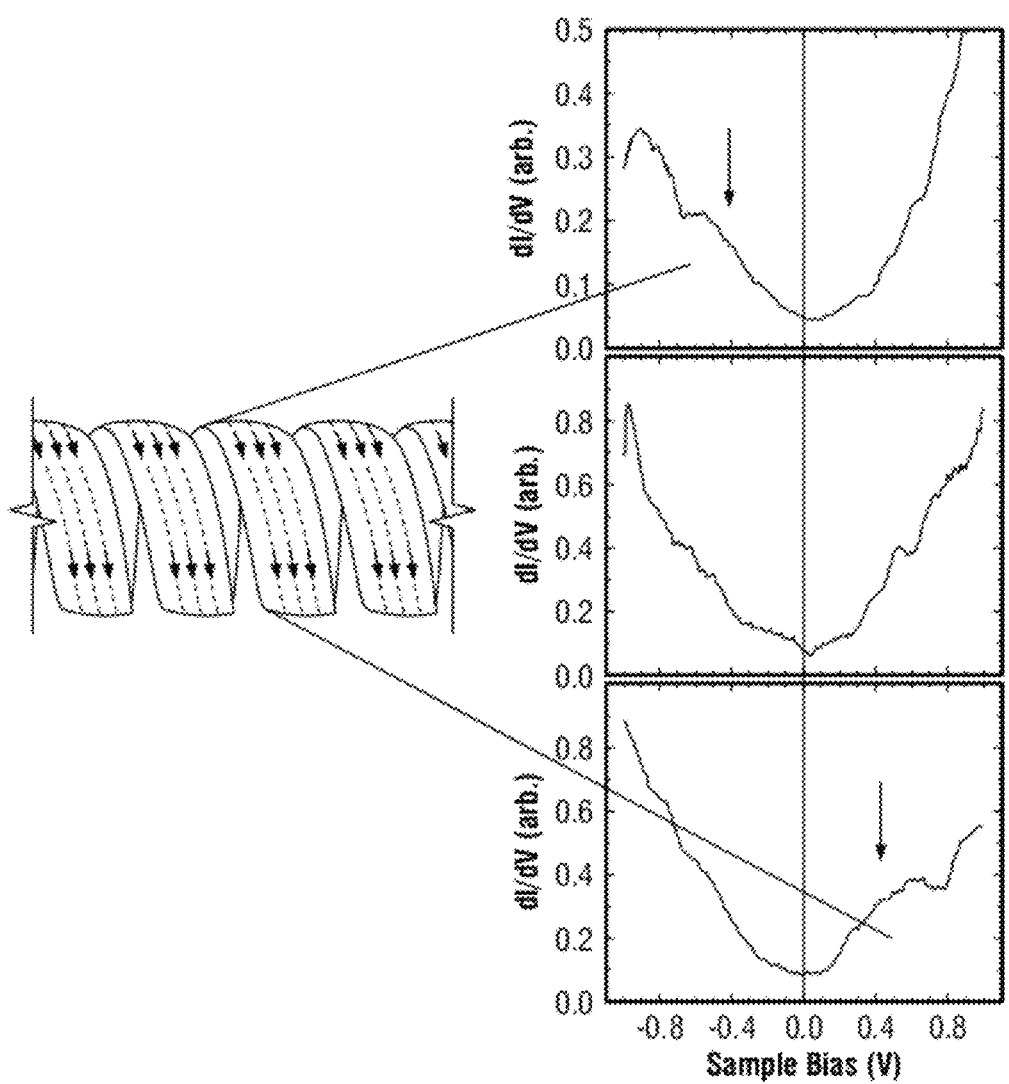
FIG. 10 is a schematic of a likely charge path of the purified nanowire of FIG. 9 (left) according to an embodiment.

Although the STM measurements show the density of states in the transverse direction (lateral conductivity), this behavior is consistent with rectifying behavior in the longitudinal direction (axial conductivity). This is illustrated schematically in FIG. 10. If the microbial nanowires were ohmic conductors, the plot would have been symmetrical. FIG. 10 also shows a likely charge path in the purified nanowire of FIG. 9 (left). The enhanced density of states on opposite edges is consistent with rectifying behavior in the axial direction, given the likely helical path of current flow along the pilus.

The purified nanowires used in this example lack metals and are not associated with any redox protein or cofactor, as discussed above in Example 1. Thus, the molecular rectifying behavior of microbial nanowires is a consequence of the biochemical nature of the nanowire (protein amino acid composition, structure, and chemical modifications). Because of this, genetic engineering can be used to modify the native rectification properties to produce customized rectifiers with electronic properties suitable for each particular application. The proteinaceous nature of these microbial rectifiers also makes them biodegradable and desirable for applications in nanomedicine. Furthermore, mass-production in recombinant hosts and in vitro assembly also is possible to reduce the cost associated with their synthesis. Additional testing will include two-probe and four-probe devices.

EXAMPLE 3

To determine yields, cultures were grown at 25° C. according to the methods described in the above examples to induce the expression of nanowires. Cultures were also grown at 30° C. to produce otherwise identical cells, but without the nanowires.

The resulting cells were lyzed and total cell protein was calculated for samples having a similar OD at approximately 600 nm, thus similar number of cells.

Although the expression of the nanowires changed, the total cell protein did not substantially change in these two cultures. For this reason, the 30° C. protein value was subtracted from the 25° C. value, with the resulting value used as the amount of protein corresponding to the nanowire in the starting culture. Protein assays to the purified nanowires resulting from the 25° C. culture were also performed.

The resulting yield was approximately 63%. It is likely that yields can be even higher with improved methods or with more accurate assays of pili production in the starting cultures.

EXAMPLE 4

Method II for Purifying Pili to Homogeneity

In this example, pili, purified as assemblies of a single peptide subunit, the PilA pilin, and without any associated proteins, such as c-cytochromes, or metals are shown to be conductive. Metals, ions and other known redox cofactors such as flavins and quinones were also absent.

Starting Materials

The starting materials as well as the bacterial strains and culture conditions were as described in Example 1.

Isolation and Purification of Pili

Pili were purified to homogeneity as described in Example 1 except that all the buffers used during the purification contained 1 mM ethylenediaminetetraacetic acid (EDTA) and all drying steps were carried out with a constant flow of filter-sterilized $N_2$ gas rather than in a Speed Vac (which may introduce contaminants in the pili samples).

Unless otherwise indicated, dried preparations of purified pili were resuspended in 10 mM CHES buffer containing 1 mM EDTA and incubated for a minimum of 24 h at 4° C. to deaggregate the pili bundles that formed during purification. A 2:1 (v/v) chloroform-methanol solution was then added to the pili samples to extract quinone-like contaminants following the method in F. Brito, J. A. DeMoss, M. Dubourdieu, *J. Bacteriol.* 177, 3728 (July 1995). After 2 h at 4° C., the chloroform phase was removed and discarded. The methanol was then evaporated with a constant flow of filter-sterilized $N_2$ gas and the dry pili sample was stored at −20° C. for short-term use or flash frozen in liquid nitrogen and stored at −80° C. for long-term use.

*Pseudomonas aeruginosa* strain K (PAK) pili were purified as described in W. Paranchych et al., *Can. J. Microbiol.* 25, 1175 (October 1979), with some modifications. Briefly, PAK cultures grown in TBS to late-exponential phase were plated on TBS agar plates and grown overnight at 37° C. The cells were harvested from the plates and suspended in standard saline citrate buffer, SSC (1 g of wet weight per 10 ml SSC). Pili and flagella were sheared off the cells mechanically by stirring the cell suspension at 4° C. for 2 h and vortexing 5 times (1 min each cycle). Bacterial cells were removed by centrifugation (8000×g, 20 min). Pili and flagella were precipitated out of the supernatant fractions with NaCl (0.5 M) and polyethylene glycol 6000 (PEG 6000, 1% w/v) after overnight incubation at 4° C. The pili and flagella precipitates were harvested by centrifugation (6000×g, 25 min) and separated after incubating the samples at 4° C. in a 10% w/v $(NH_4)_2SO_4$ solution (pH 4.0) for 2 h. After centrifugation (6000×g for 15 min), the supernatant fraction containing the flagella was discarded. Three sequential steps of ammonium sulfate precipitation were used to remove any remaining flagella from the pili samples. The final pellet, containing the purified PAK pili, was resuspended in $ddH_2O$ and dialyzed for 24 h to remove any remaining $(NH_4)_2SO_4$. The dyalized solution was used for STM experiments Protein concentration in the pili preparations was determined with the bichinchoninic acid (BCA) assay (S8) (Pierce®, Thermo Scientific) and using 60° C. incubations for 1 h. Bovine Serum Albumin (BSA) was used as the protein standard.

Microscopy

Transmission Electron Microscopy (TEM)

Purified pili were resuspended in $ddH_2O$ (adjusted to pH 7) to visualize the pili bundles or in 10 mM CHES buffer (pH 9.5) and incubated at room temperature for 72 h to promote deaggregation. These samples were adsorbed onto a 300-mesh carbon-copper grids (Electron Microscopy Sciences), negatively stained with 1% (w/v) uranyl acetate, and allowed to dry, as described in Example 1. The samples were examined with a Jeol 100 CX electron microscope (Japan Electron Optic Laboratory) operated at 100 kV.

Scanning Probe Microscopy

Pili samples were routinely deposited on freshly cleaved highly oriented pyrolytic graphite (HOPG) and imaged with an atomic force microscope (AFM), as described in Example 1. Distal (lateral) and axial (length) conductivity measurements were performed by scanning tunneling microscopy (STM) and conductive probe-AFM (CP-AFM), respectively. For STM, dried preparations of G. sulfurreducens or PAK pili were resuspended in phosphate buffer saline (PBS) and deposited for 15-30 min. The excess liquid was wicked with absorbent paper and the HOPG surface was dry under a stream of $N_2$ gas. Applying a voltage with the STM causes electrons to tunnel from occupied states at the sample surface into unoccupied states of the tip, or vice versa. As the amount of tunneling current is proportional to the number of available electronic states, STM was used to probe the local density of states of the pili. This technique also provides a higher spatial resolution probe and more direct electronic characterization compared to conventional conducting probe-atomic force microscopy (CP-AFM) approaches.

Scanning Tunneling Microscopy (STM)

STM images were acquired at constant sample voltages, as indicated, by scanning while keeping the tunneling current constant with the use of a feedback circuit. The apparent STM width of the pilus fibers was obtained from cross sections and the broadening effect was corrected as described in Biró, L. P et al. 1998. Scanning tunneling microscopy (STM) imaging of carbon nanotubes. Carbon 36:689-696. The axial electronic structure of the pilus fiber imaged by STM was also generated to identify electronic (voltage-dependent) and topographic (present at all voltages) periodicities. I-V curves were obtained with the tip positioned on the center of the pilus filaments while suspending the feedback and ramping the bias voltage.

The tunneling conductance, $dI/dV$, was calculated as the numerical differentiation of the I over V values and plotted against the tip-sample bias (voltage, V) to investigate the density of states of the G. sulfurreducens pili as a function of energy and in reference to the PAK pili controls.

Conducting Probe-Atomic Force Microscopy (CP-AFM)

Conducting probe-atomic force microscopy (CP-AFM) was used to probe the axial conductivity of the G. sulfurreducens pili with a Bio-AFM-CF instrument (Asylum). The substrate used for pilus deposition and measurements was a gold electrode grid nanofabricated onto a silicon substrate. For the fabrication of the gold grid, photoresist (Shipley S1813) was spin-coated onto silicon wafers having a 300 nm thermal oxide layer ($SiO_2$).

After photoresist development, patterned gold electrodes were deposited by thermally evaporating 5 nm of titanium followed by 25 nm of gold onto the surface of the wafer. A solution containing ca. 5 µg/ml of purified pili in dd$H_2$O with 1 mM EDTA was then deposited onto the electrodes, left to adsorb for 10-20 min, and then wicked dry with absorbent paper. CP-AFM was performed with Pt-coated cantilevers having spring constant 2 N/m (Veeco).

Pilus nanowires lying across the gold-$SiO_2$ interface were first identified in imaging mode. For I-V measurements, the tip was placed on a point of the pilus lying on the $SiO_2$. Positive controls were generated by positioning the tip on the gold electrode, while negative controls were produced by positioning the tip on the $SiO_2$ substrate at 100-nm distances from the gold edge. The resistance of the pilus was calculated from the slope of the linear current-voltage (I-V) plot. Ohm's law ($I=V/R$) was used to estimate the current (in Amps) along the pilus. If a potential of 100 mV were applied across the length of this pilus, the current would be $I=V/R=1e-1/2e8=5e-9=5$ nano amps ($=5$ nA).

Protein Electrophoresis and Immunoblot Analyses

Dried preparations of purified pili were resuspended in 5 ml of dd$H_2$O containing 10% (w/v) Octyl-b-D-Glucopyranoside (OG) (Sigma) and incubated at room temperature for 2 h. The concentration of OG was adjusted to 2% (v/v) and the solution was incubated for an additional 24 h at room temperature prior to SDS-PAGE. The OG-treated sample was boiled in SDS-PAGE sample buffer (S9) and subjected to electrophoresis on 10-20% Tris/Tricine ReadyGels (Bio-rad) using a Mini Protean Tetra Cell apparatus (Bio-Rad). After SDS-PAGE separation, the proteins in the gel were electrophoretically transferred to a PVDF membrane (HyBond LFP™, Amersham GE Healthcare) at 25 V for 150 min using a Mini Protean Tetra Cell apparatus (Bio-rad).

The Amersham ECL Plex Western blotting kit was used for the electrophoretic transfer and membrane blocking, following manufacturer's recommendations. After blocking, the membrane was incubated for 90 min at room temperature and with gentle agitation in 10 ml of an antibody solution containing a 1:5,000 dilution of the primary antibody (rabbit anti-PilA polyclonal antibodies raised against the 42 amino acids at the carboxy-terminus of the PilA protein) and a 1:2,500 dilution of goat anti-rabbit IgG antibodies conjugated to the $Cy^{tm}$ 5 fluorescence dye (ECL™ Plex, Amersham GE Healthcare). The membrane was washed 4 times (5 min each) in wash buffer (TBS-T, pH 7.4, 0.1% Tween 20) and rinsed three times in wash buffer without Tween 20.

The protein bands that hybridized with the anti-PilA antibodies were visualized after scanning the blot with a Typhoon imager (GE Healthcare Sciences) operated in fluorescence mode (excitation at 633 nm, 670 BP 30 filter, and PMT setting at 600 V).

Elemental Analyses

The SeqCHED web server (R. Levy, M. Edelman, V. Sobolev, Proteins 76, 365 (Aug. 1, 2009) within the SPACE tools suite (V. Sobolev et al., Nucleic Acids Res. 33, W39 (Jul. 1, 2005)) of the Weizmann Institute of Science were used to identify conserved metal-ion binding sites in the translated gene sequence of the pilA gene (GSU1496) of G. sulfurreducens. The amino acid sequence of the mature, processed pilin (starting at phenylalanine in position 11 (FIG. 12), rather than the full length precursor, was used for these analyses. Information about this application and the metal-binding prediction algorithm can be found at http://ligin.weizmann.ac.il/seqched/.

Quantitative elemental analysis of the purified pili preparations was performed by Inductively Coupled Plasma-Atomic Emission Spectrometry (ICP-AES) using a Thermo Jarrell-Ash Enviro 36 Inductively Coupled Argon Plasm (Chemical Analysis Laboratory, University of Georgia, Athens). For these experiments, samples of purified pili (ca. 15 µg/ml) were resuspended in 10 mM CHES buffer (pH 9.5, 1 mM EDTA) and analyzed in reference to blank control samples (same buffer without protein). The Lowest instrumental Limits of Detection (LOD) shown in Table 4 were obtained from the CAIS website, http://www.uga.edu/cais/analytical_services/chemical_analysis/elements2.htm. The LOD values and measurements (in ppm) were used to calculate the amount of atoms per pilin subunit.

TABLE 4

Lowest Instrumental Limits of Detection (LOD)

| Elemental analyses of *G. sulfurreducens* | LOD[a] ppm | LOD[a] atoms/pilin | Pili elements (atoms/pilin)[b] |
|---|---|---|---|
| Al | 0.06 | 2.9 ± 0.9 | <LOD |
| Sb | 0.09 | 6.9 ± 2.1 | <LOD |
| As | 0.08 | 3.3 ± 1.0 | <LOD |
| Ba | 0.06 | 28.5 ± 8.6 | <LOD |
| Be | 0.09 | 1.3 ± 0.4 | <LOD |
| B | 0.10 | 31 ± 9.3 | <LOD |
| Cd | 0.06 | 3.8 ± 1.2 | <LOD |
| Cr | 0.06 | 3.1 ± 0.9 | <LOD |
| Co | 0.06 | 3.6 ± 1.1 | <LOD |
| Cu | 0.07 | 3.4 ± 1.0 | <LOD |
| Fe | 0.05 | 2.8 ± 0.8 | <LOD |
| Pb | 0.06 | 39.5 ± 11.9 | <LOD |
| Mg | 0.03 | 3.8 ± 1.1 | <LOD |
| Mn | 0.10 | 5.6 ± 1.7 | <LOD |
| Mo | 0.05 | 1.6 ± 0.5 | <LOD |
| Ni | 0.10 | 67.1 ± 20.2 | <LOD |
| P | 0.09 | 5.3 ± 1.6 | <LOD |
| K | 0.50 | 9.0 ± 2.7 | <LOD |
| Se | 0.09 | 0.9 ± 0.3 | <LOD |
| Si | 0.50 | 2.3 ± 0.7 | <LOD |
| Ag | 0.10 | 3.5 ± 1.1 | <LOD |
| Na | 0.50 | 54.9 ± 16.5 | <LOD |
| Sr | 0.05 | 1.8 ± 0.5 | <LOD |
| V | 0.15 | 9.1 ± 2.7 | <LOD |
| Zn | 0.05 | 2.4 ± 0.7 | <LOD |

[a] Lowest instrumental Limits of Detection (LOD)
[b] Average value and standard deviation of three biological replicates.

UV-VIS Absorption and Fluorescence Spectroscopy

Dry purified pili samples were resuspended in ½ volume of isopropanol and, then, ½ volume of ddH$_2$O, Standards with L-tyrosine, riboflavin and menaquinone were also prepared as solutions in isopropanol and ddH$_2$O, as described for the pili samples. Absorption spectra were collected with a Cary100 UV-Vis spectrometer (Varian) set to 2 nm bandpass. Fluorescence spectra were measured with QuantaMaster spectrometer (Photon Technology International), with 270 nm excitation and 5 nm bandpass. All spectra were collected at room temperature, in quartz cuvettes with 1 cm path length (Spectrocell Inc.)

Calculation of Fe(III) Oxide Respiratory Rates

Using rates of Fe(III) oxide reduction (measured as the production of Fe(II)) and cell growth (measured as number of cells from cultures doubling every 15 h) reported in G. Reguera et al., *Nature* 435, 1098 (Jun. 23, 2005), the electron transport rates per cell were inferred. From the linearity of Fe(II) production during the reduction of Fe(III) oxides, electron transport rates of $5 \times 10^{12}$ electrons per second were calculated. After dividing this number by the culture's growth yield ($5 \times 10^7$ cells after the reduction of ca. 40 mM of Fe(III) oxides) a respiratory rate of ~$10^5$ electrons per cell per second was estimated.

Despite the absence of mediators, the protein matrix conducted electrons axially and at rates several orders of magnitude above those measured during the respiration of Fe(III) oxides. These distances and rates greatly exceed the known limits for charge transport reactions through protein matrices and make the pilus nanowires a new paradigm in protein electron transfer.

Results

Figure 11A:
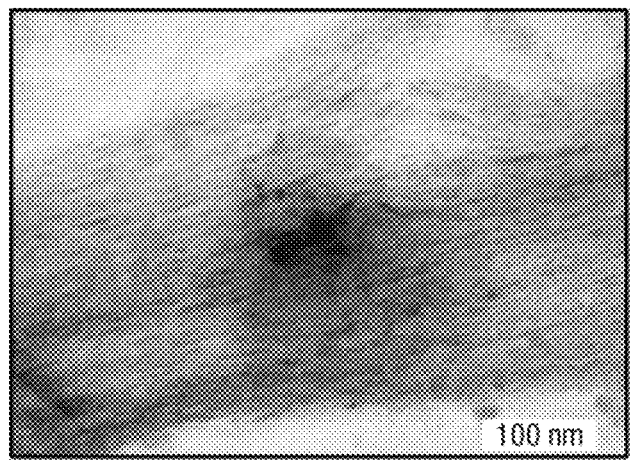
FIG. 11A is a TEM micrograph of negatively stained *G. sulfurreducens* pili purified as thick bundles at pH 7 according to an embodiment.
Figure 11B:
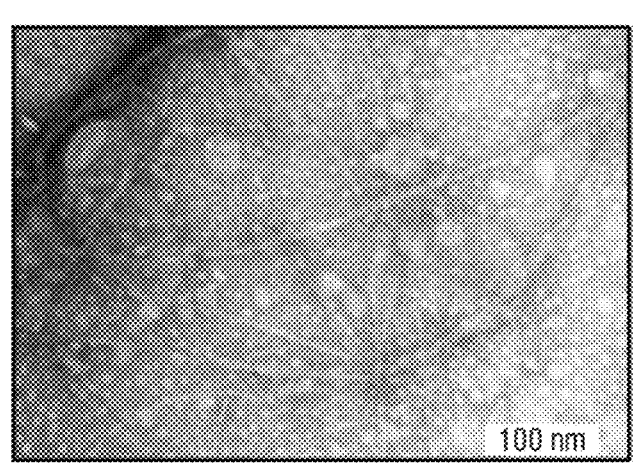
FIG. 11B is a TEM micrograph of negatively stained *G. sulfurreducens* pili deaggregated into individual pilus filaments at pH 9.5 according to an embodiment.

Electrostatic interactions between the pili during their purification at neutral pH resulted in thick bundles or ropes that did not solubilize in SDS and enabled their purification (FIG. 11A). These intermolecular interactions were effectively destabilized at basic pH and enabled the separation of the individual pilus fibers (FIG. 11B).

Figure 11C:
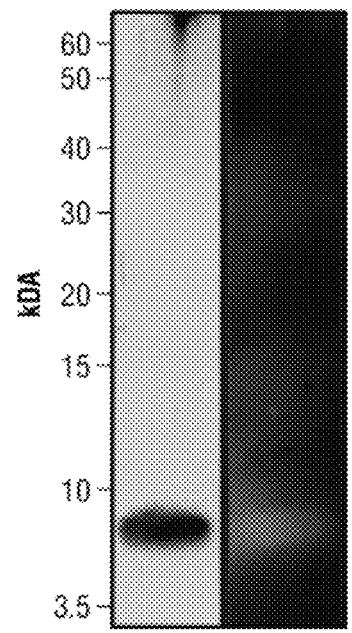
FIG. 11C shows a silver-stained SDS-PAGE (left panel) to octyl-glucoside-depolymerized pili showing the 6.5 kDa PilA protein band and immunoblot (right panel) showing its hybridization with anti-PilA polyclonal antibodies according to various embodiments.

The biochemical composition of the pili was analyzed by fully depolymerizing the fibers with octyl-glucoside and separated the pilus' protein components by denaturing SDS-PAGE. The depolymerization yielded a single peptide subunit with the apparent mass (ca. 6.5 kDa) expected for the mature PilA pilin and hybridized with anti-PilA antibodies (FIG. 11C). OmcS, a 50-kDa outer membrane c-ytochrome which has been hypothesized in C. Leang, X. Qian, T. Mester, D. R. Lovley, *Appl. Environ. Microbiol.* 76, 4080 (June 2010) to adsorb to pili-like filaments in *G. sulfurreducens* and mediate conduction, was successfully removed during the purification.

Figure 12A:
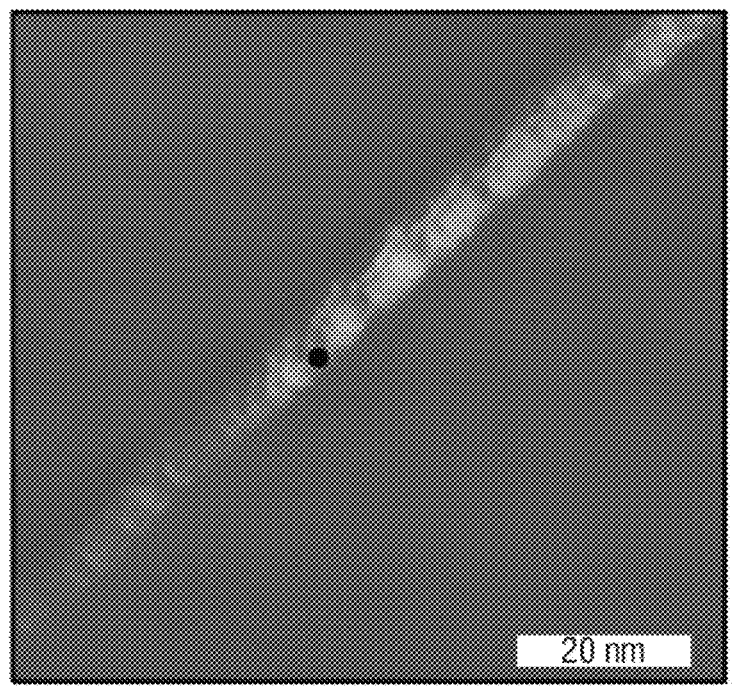
FIG. 12A is a STM topographical image of *G. sulfurreducens* acquired using 0.5 V and 100 pA according to an embodiment.
Figure 12B:
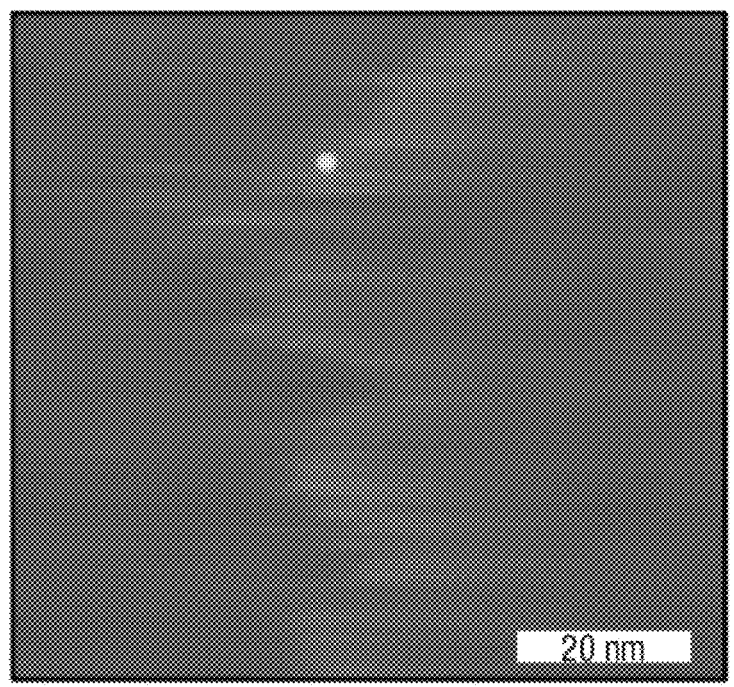
FIG. 12B is a STM topographical image of PAK pili acquired at 3.0 V and 45 pA according to an embodiment.
Figure 12C:
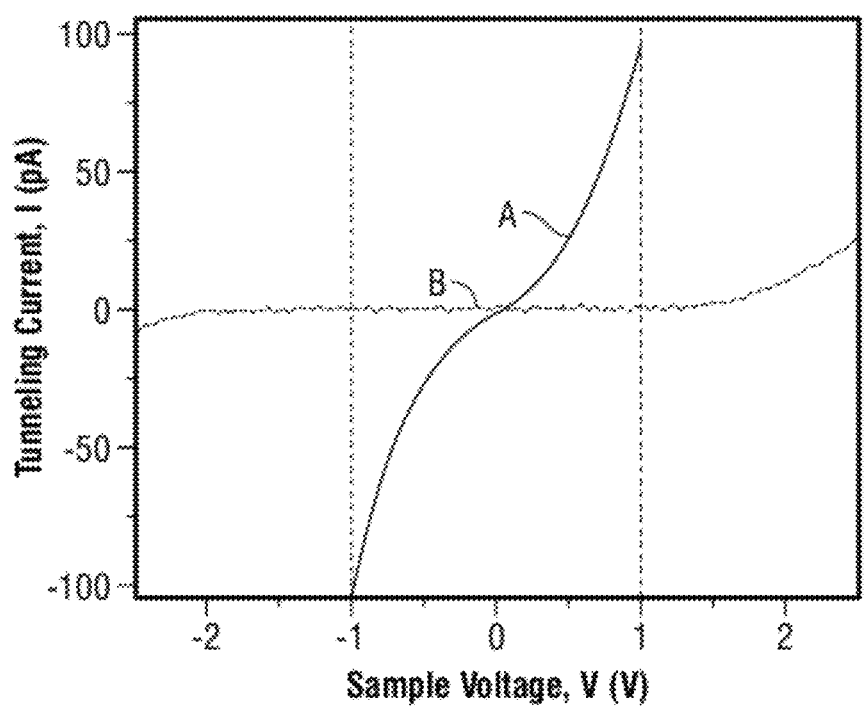
FIG. 12C shows STM I-V curves "A" and "B" acquired at pili locations indicated by black dot in FIG. 12A (curve "A") and gray dot in FIG. 12B (curve "B") according to various embodiments.

Despite the absence of proteins other than the PilA subunit, the pili were conductive by scanning tunneling microscopy (STM) (FIGS. 12A-12C). STM imaging of the purified pili showed conducting filaments with periodic molecular substructures, corresponding to regions of the pilus that supply more tunneling current due to an increase in the local density of states (FIG. 12A).

Figure 13:
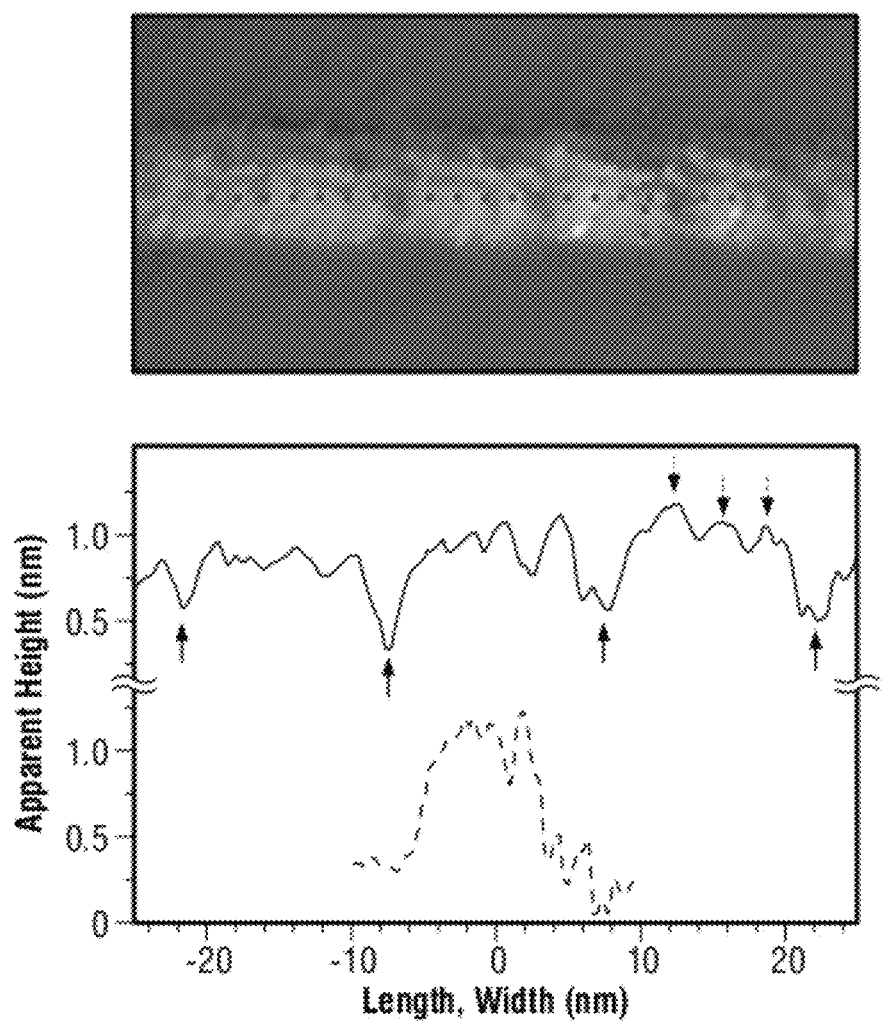
FIG. 13 is a STM topographical image (top) and height measurements (bottom) of a section of the pilus fiber shown in FIG. 2C acquired in constant current mode (0.5V, 100 pA) according to various embodiments.

FIG. 13 shows a STM topographical image (top) and height measurements (bottom) of a section of pilus fiber produced according to the method described in this Example and acquired in constant current mode (0.5V, 100 pA). The height graph, at the bottom, shows a large (ca. 10 nm) apparent width of the pilus fiber (lower curve), due to the distortion caused by the broadening effect of the tip as it crosses the pilus. The axial length measurements (upper curve) show voltage-dependent features every 14 nm (upward pointing arrows) and topographical peaks every 2-3 nm (downward pointing arrows). The axial periodicity included deep 14-nm repeating electronic features interspersed with 3-4 nm periodic topographic substructures (FIG. 13). The apparent STM width was ca. 10 nm (FIG. 13), yet produced ca. 5 nm widths once the distortion caused by the broadening effect of the tip while traversing the fiber was subtracted.

In contrast, pili purified from *Pseudomonas aeruginosa* strain K (PAK) were insulators in the ±1 V range and could only be imaged at large sample voltages (greater than 2 V) and low tunneling current set points (FIG. 12B). At these voltages, tip instabilities often result due to the large electric field between the tip and the sample, which causes distortions and noise in the imaged data. I-V (current vs. voltage) measurements taken at fixed locations of the pilus filaments confirmed the metallic (ohmic) behavior of the *G. sulfurreducens* pili at biological (±1 V) voltages and the insulating behavior of the PAK pili (FIG. 12C).

Figure 14A:
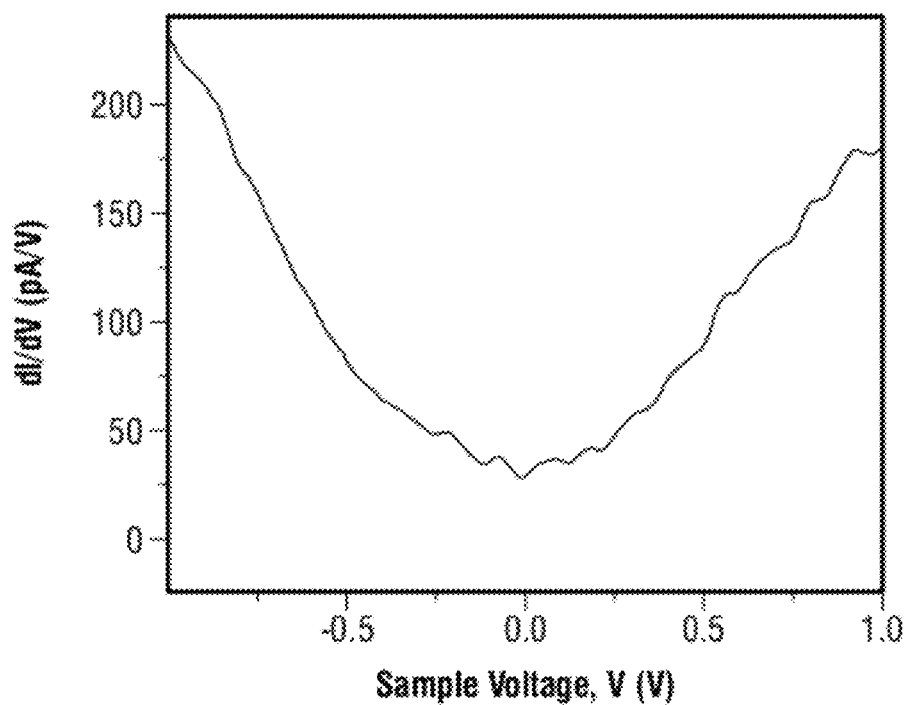
FIGS. 14A and 14B show tunneling conductance, dI/dV, of the *G. sulfurreducens* pili (FIG. 14A) and the PAK pili controls (FIG. 14B) according to various embodiments.
Figure 14B:
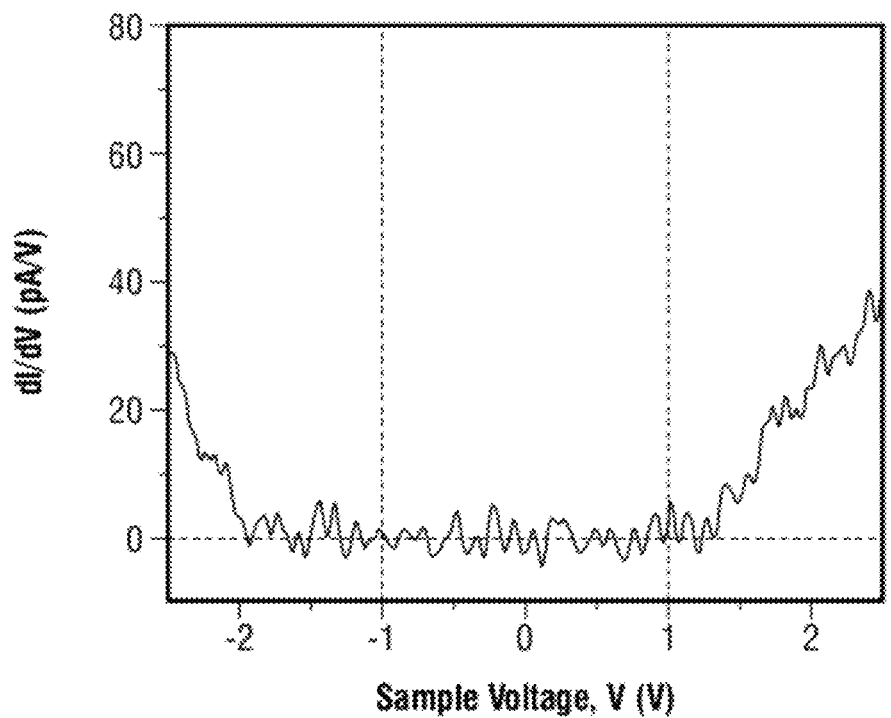

FIGS. 14A and 14B show tunneling conductance, dI/dV, of the *G. sulfurreducens* pili (FIG. 14A) and the PAK pili controls (FIG. 14B) obtained as the numerical differentiation of the I and V values shown in FIG. 12C and plotted against the tip-sample bias voltage (V). As FIG. 14A shows, the *G. sulfurreducens* pili produced a conductor-like spectrum with electronic states at low voltages, never reaching zero conductance. Furthermore, the plot of the conductance, dI/dV, versus the tip-sample bias voltage, V, revealed clear electronic states at low voltages, never reaching zero conductance in the *G. sulfurreducens* pili, which is consistent with the behavior of a true conductor. This is in contrast to the insulator-type spectrum of the PAK pili characterized by a large (±1.5-2 V) band gap at zero conductance (FIG. 14B). The STM analyses thus confirmed the unique electronic structure of the pili of *G. sulfurreducens* that enables them to function as electronic conduits.

The lack of proteins, other than the PilA pilin, in the purified pili excluded any contribution from c-cytochromes to its conductivity but did not exclude the possibility of metal mediators. Metals can bind to conserved structural protein motifs and mediate electron transfer reactions while stabilizing the protein's secondary structure. Although the predictive features of the SeqCHED server did not identify any conserved metal-ion binding sites in the PilA peptide subunit, the assembly of pilins in the pilus shaft could create structural and sequence motifs for metal coordination. Thus, we analyzed the elemental composition of the pili by inductively coupled plasma-atomic emission spectroscopy (ICP-AES).

Despite the high specificity and sensitivity of this technique at the identification and quantification of trace elements, inorganic elements known to catalyze electron transfer (Fe, Cu, Mo) and redox catalysis (V, Mn, Fe, Co, Ni, Cu and W) in biological systems were below detection limits (Table 4). Low levels of $Ca^{2+}$ were detected (1.7±0.9 atoms of $Ca^{2+}$ per pilin subunit), consistent with the known affinity of purified pili for this cation as discussed in J. C. McMichael, J. T. Ou, *J. Bacteriol.* 138, 976 (June 1979) and its role at neutralizing the electrostatic interactions that promote pili aggregation (See L. Craig et al., *Mol. Cell.* 23, 651 (Sep. 1, 2006)). This is in agreement with the biological role of $Ca^{2+}$ atoms at balancing charges in proteins as discussed in K. L. Haas, K. J. Franz, *Chem. Rev.* 109, 4921 (October 2009).

Flavin cofactors, such as flavin mononucleotide (FMN) or flavin adenosyl dinucleotide (FAD), can also bind proteins and enable electron transfer and redox reactions. The presence of flavins in the pilus protein was investigated by UV-visible spectroscopy, based on the ability of the flavin's isoalloxazine ring to absorb light in the UV and visible spectral range. Quinones, such as ubiquinones and menaquinones, function as lipid soluble electron carriers between membrane-bound respiratory complexes, due to their ability to bind specific structural motifs in hydrophobic regions of quinone-reactive redox proteins. Type IV pili are anchored on the inner membrane of Gram-negative bacteria where they can accept quinones from the membrane-bound menaquinone pool. They also have a narrow (6-11 Å) hydrophobic central channel that could potentially house quinones and create an internal pathway for electron transfer free of solvents.

Figure 15A:
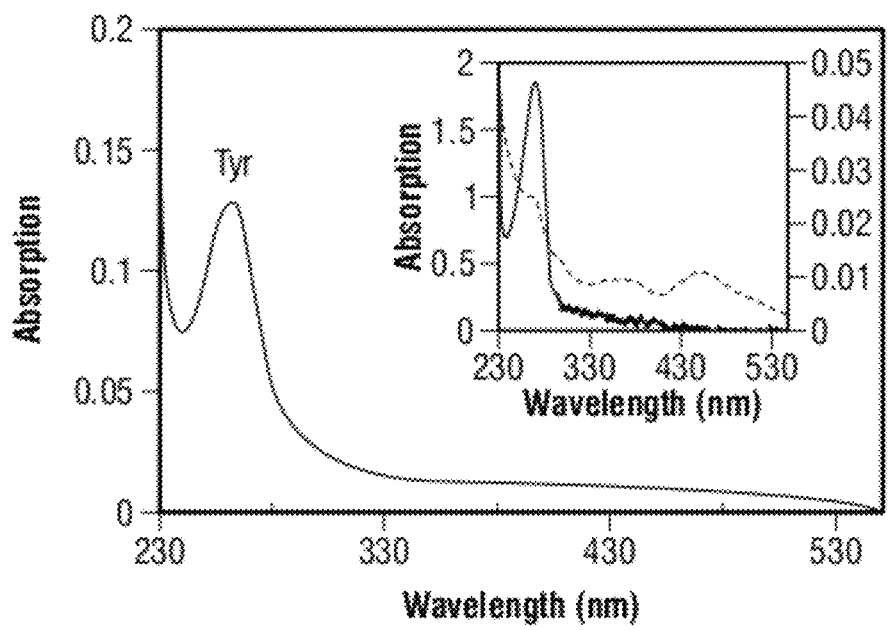
FIG. 15A shows an absorption spectrum of purified *G. sulfurreducens* pili and, in the inset, the spectrum is shown in comparison to a standard according to an embodiment.

The purified pili absorbed strongly below 230 nm and at ~270 nm. FIG. 15A shows an absorption spectrum of the purified pili. The inset in FIG. 15A shows the same pili spectrum in comparison to riboflavin (dashed line), where the axes have been adjusted to scale.

Figure 15B:
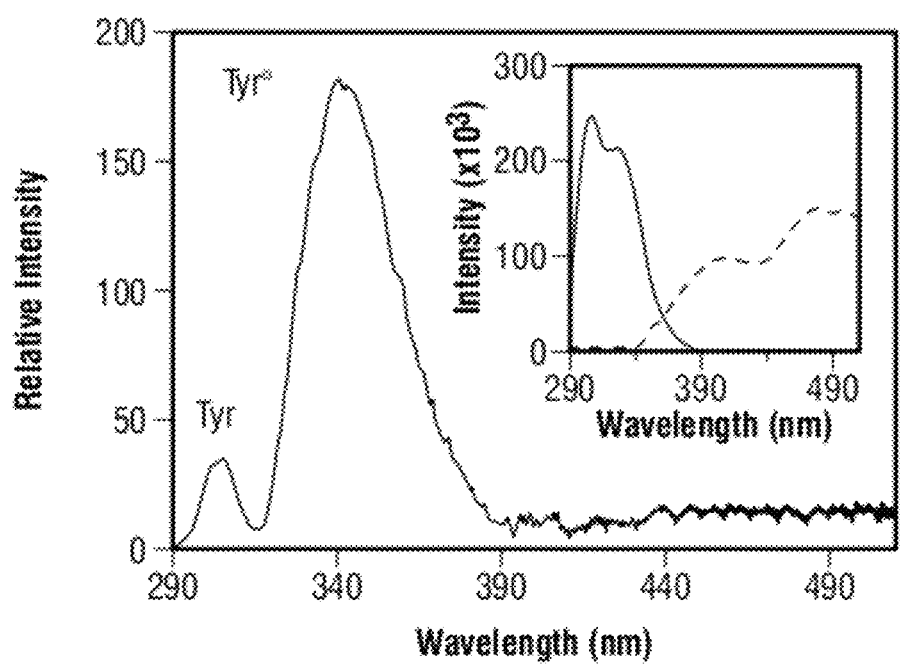
FIG. 15B shows a fluorescence spectrum of purified *G. sulfurreducens* pili, and in the inset, the fluorescent spectra of L-tyrosine (solid line) and menaquinone (dashed line) according to an embodiment.

FIG. 15B shows a fluorescence spectrum of the purified pili, where the inset shows fluorescence intensity as relative fluorescence units corrected by a factor of $10^3$ with L-tyrosine (solid line) and menaquinone (dashed line) spectra. As with UV-VIS spectroscopy, the fluorescence emission from the pilin's tyrosines was used as a marker for the pilus protein in reference to an L-tyrosine standard solution.

The pili spectrum produced two single peaks at ca. 300 and 340 nm, corresponding to the excitation peaks of tyrosine and its ionized form, tyrosinate, respectively. Ionization of the phenolic hydroxyl group in tyrosine is generated by a carboxylate group of a nearby aspartic or glutamic amino acid.

Note that Tyrosines yield two fluorescence peaks corresponding to the tyrosine (Tyr) and tyrosinate (Tyr•) forms (FIG. 15B). These fluorescent spectra are consistent with the emission from peptide bonds and the pilin's tyrosine residues (FIG. 16). Thus, the strong tyrosinate peak detected in the pili spectrum reflects the contribution of neighboring acidic residues (3 aspartic and 2 glutamic residues in the pilin, as shown in FIG. 16). Such emission is also generally discussed in C. R. Cantor, P. R. Schimmel, *Techniques for the study of biological structure and function*. Biophysical Chemistry vol. 2 (W. H. Freeman, San Francisco, 1980).

Notably, the pili spectra had no peaks in the visible region (at ~360 and ~450 nm) where flavins absorb. These results demonstrate that the pili are not flavoproteins. Coincidentally, flavins can also fluoresce at 440-470 nm wavelengths or higher (FIG. 15C), depending on the type of flavin cofactor and the nature of the flavin-binding site in the protein. However, despite their high quantum yield compared to tyrosines, flavins were not detected in the pili spectrum, thus providing additional, confirmatory evidence for the absence of flavins in the pili. The fluorescence spectrum also had no peaks above 390 nm, which are the wavelengths for quinone emission (FIG. 15B (inset)).

The finding that the *G. sulfurreducens* pili are conductive in the absence of other proteins and organic or inorganic cofactors demonstrates that the protein matrix is responsible for its conductance. Although electrons can travel through protein matrices, distance is limited to the <14 Å separation between the protein's redox centers that is required for optimal electron tunneling. The observed transport of electrons across the ca. 5-nm pilus width (FIGS. 12A-12C) suggests that the pilus protein assembly could enable charge transport at greater distances.

Figure 17A:
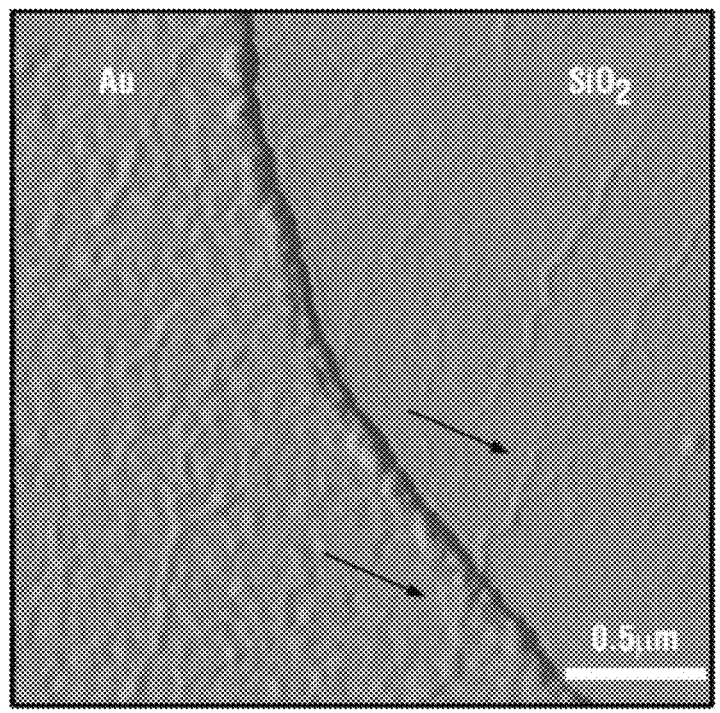
FIG. 17A is an AFM image of pili deposited onto a 25-nm thick gold electrode nanofabricated onto an insulating $SiO_2$ surface according to an embodiment.
Figure 17B:
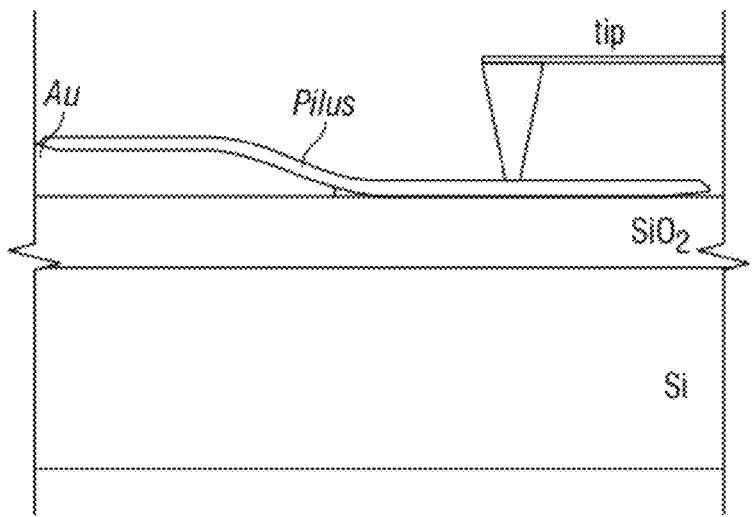
FIG. 17B is a schematic of a two-point transport measurement between the gold electrode and a CP-AFM tip through a pilus filament according to an embodiment.
Figure 17C:
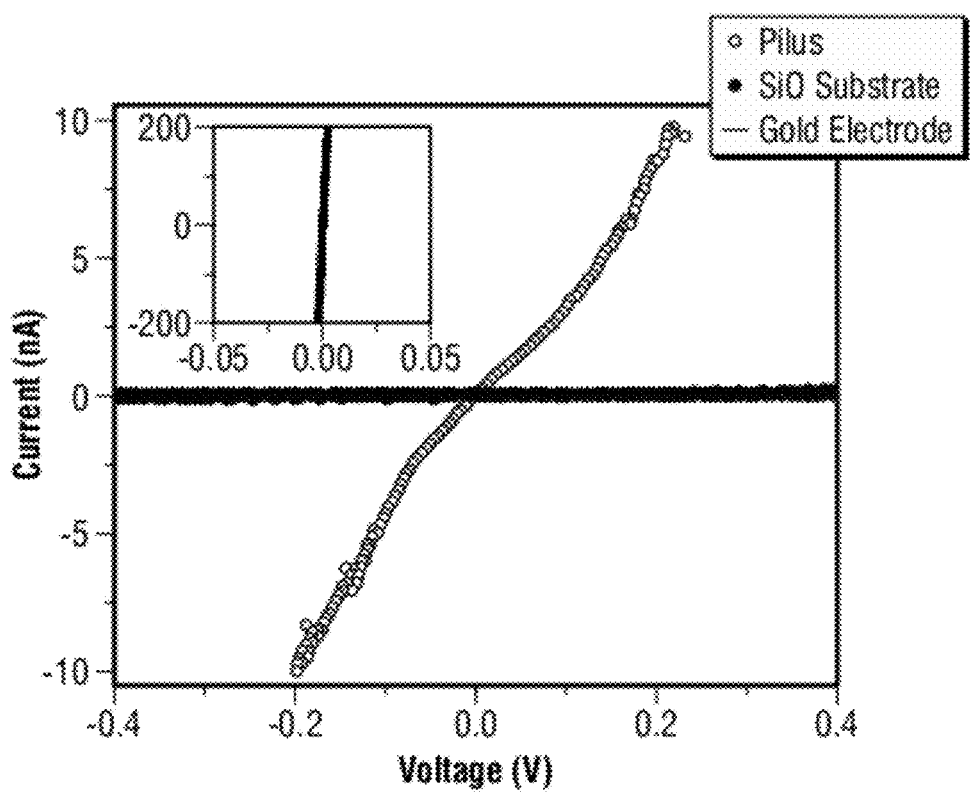
FIG. 17C show I-V (current-voltage) curves obtained with CP-AFM according to various embodiments.

To further investigate this possibility, CP-AFM was used to measure the axial conductivity of individual pilus fibers deposited on gold electrodes nanofabricated onto an insulating $SiO_2$ substrate. FIG. 17A is an AFM image of pili deposited onto a 25-nm thick gold electrode nanofabricated onto an insulating $SiO_2$ surface with the arrows pointing to an example where a pilus clearly overlaps the edge of the gold electrode. FIG. 17B is a schematic of a two-point transport measurement between the gold electrode and a CP-AFM tip through a pilus filament. FIG. 17C show I-V (current-voltage) curves obtained with CP-AFM. The curve taken with the tip positioned on a pilus (red) was acquired at a location about 200 nm from the gold electrode. In contrast, negligible current was detected with the same tip in contact with the substrate at 100 nm from the gold edge (black). The inset shows data acquired with the same tip in contact with the gold electrode, with the same vertical and horizontal units as the large plot.

The current was linear when the tip was positioned on a pilus filament at 200-nm distances from the gold edge, while no current was detected when the tip was positioned on the silicon substrate at 100-nm distances from the gold edge. A resistance R=200 MΩ was measured along a 1 μm-long pilus and an electron transport rate of $3.1 \times 10^9$ electrons per second at a potential of 100 mV. The measured resistivity (ρ, "rho") was 0.4 Ω·cm. This number is less than half the lowest resistivity (1 Ω·cm) measured for *Shewanella* nanowires as discussed in M. Y. El-Naggar et al., *Proc. Natl. Acad. Sci. USA* 107, 18127 (Oct. 19, 2010), which rely on c-cytochromes for long-range electron transport as discussed in Y. A. Gorby et al., *Proc. Natl. Acad. Sci. USA* 103, 11358 (Jul. 25, 2006), and is even lower than moderately doped silicon nanowires (0.5 Ω·cm).

Based on the linearity of Fe(II) production and cell growth yields during the reduction of Fe(III) oxides by *G. sulfurreducens* respiratory rates of ~$10^5$ electrons per cell per second were calculated. These rates are several orders of magnitude lower than the rates of electron transport measured along the pilus. Thus, a single cell could discharge all the respiratory electrons onto the Fe(III) oxides with only one pilus. Yet cells from Fe(III) oxides cultures display several (>10) pili on one side of the cell, consistent with a biological strategy that maximizes the redox active surface of the cell without limiting the rate of electron transfer. Not surprisingly, adaptively evolved strains of *G. sulfurreducens* with increased rates of extracellular electron transfer also are hyperpiliated and have a reduced outer membrane c-cytochrome content.

CONCLUSION

These results demonstrate that *G. sulfurreducens* pili are protein nanowires and catalyze electron transfer reactions at rates ($\sim 10^9$ electrons per second) that do not limit the respiratory rates of the cell during the reduction of Fe(III) oxides. Contribution from other proteins and from organic and inorganic cofactors were ruled out, thus supporting a mechanism exclusively mediated by the pilus' protein assembly. A solvent-free pathway through the pilus central channel mediated by quinones was not plausible because the conductive pili had no detectable quinones. The hydrophobic nature of the pilus' inner channel also prevents solvents from filling the pilus internal cavity, which is necessary for ionic conduction through an inner electrolytic channel. Furthermore, elemental analyses by ICP-AES did not detect any ionic species such as $Na^+$, $K^+$, $Ag^+$, $Li^+$ and $Cu^+$ that could have contributed to ionic conduction in an electrolytic core or in the solid state. Biologically-relevant metals, such as Fe, Cu, Mo, V, Mn, Co, Ni, and W, which are involved in biological electron transfer or redox processes, or metal dopants, such as B and Cd, which are commonly used to metalize insulating materials and inorganic nanowires were also below the limits of detection.

The ICP-AES technique used in this study had the sensitivity to detect several atoms of metals per pilin (Table 4). With an estimated distance of 10.5 Å between pilin heads in the pilus shaft, it would have taken at least one metal atom per assembled subunit to maintain optimal (<14 Å) tunneling distances. Yet despite the lack of metals, the pilus nanowires displayed metallic-like properties.

The ability of the pilus protein matrix to transport electrons over distances that greatly exceed the theoretical and experimental tunneling limits supports the involvement of multiple pathways such as multistep tunneling (hopping), single-step superexchange tunneling pathways and/or perhaps yet to be discovered transport mechanisms facilitated by the unique structural features of the *Geobacter* pilins and their assembly. The *Geobacter* pilin structure is divergent, as they lack the conserved C-t globular head of other bacterial pilins, such as the PAK pilins. This divergent structure may be adaptive and evolved in order to use the pili as electronic conduits. Furthermore, despite the structural conservation of the α1 domain (the conserved N-t 53-residue long of the α-helix that promotes hydrophobic interactions between the assembled pilins), amino acid conservation in the *Geobacter* pilins is restricted to the first 30-40 amino acids. These divergent amino acids could be positioned at optimal distances in the pilus shaft so as to provide pathways for electron transfer. Alternatively, these *Geobacter*-specific amino acids could affect subunit contacts during assembly, thereby affecting the pilus flexibility and mechanical properties so as to facilitate collision-exchange mechanisms and the electronic coupling of redox-active amino acids required for fast charge transport The finding that *G. sulfurreducens* pili are protein nanowires is significant for nanotechnological applications. The potential to customize the functional properties of proteins via well-established genetic engineering approaches far exceeds available methods for the functionalization of carbon nanotubes and inorganic nanowire surfaces. Furthermore, the conservation of the α1 assembly domain in the *Geobacter* pilins raises the possibility of mass-producing these nanowires by molecular self-assembly in a cell-free environment. This contrasts with fabrication methods for other types of nanowires, which involve high temperatures, toxic solvents, vacuums, and expensive equipment. Protein nanowires also circumvent major concerns regarding cyto- and genotoxicity that limit commercial applications of carbon, metal, and metal-oxide based nanoparticles, making them suitable for the development of biodegradable and biocompatible nanoelectronic devices and expanding the known applications of metallic nanowires.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter. For example, although the discussion herein has focused on *Geobacter sulfurreducens*, it is expected that many microorganisms which produce extracellular appendages (i.e., pili) capable of establishing a direct electrical connection with insoluble electron acceptors can be purified according to the procedures outlined herein to produce similarly functional nanowires. Such bacteria include other members of the Geobacteraceae family, but also other microbial families having this particular physiology. Therefore, it is manifestly intended that embodiments of this invention be limited only by the claims and the equivalents thereof.

What is claimed is:

1. A nanowire consisting of a purified protein filament isolated from a Geobacteraceae bacterium, wherein the purified protein filament is substantially free from contaminating proteins, metals, ions and/or redox cofactors and contains purified peptide subunits capable of assembling into the purified protein filament and establishing an electrical connection with an insoluble electron acceptor, wherein the peptide subunits are encoded by a PilA polypeptide.

2. The nanowire of claim 1 wherein the purified protein filament is a purified pilus.

3. The nanowire of claim 1 wherein the Geobacteraceae is *Geobacter sulfurreducens*.

4. The nanowire of claim 2 wherein the subunits have an approximate molecular weight of 7-kDa.

5. The nanowire of claim 1 wherein the insoluble electron acceptor is selected from Fe(III) oxide minerals, an electrode, a second purified pilus, and combinations thereof.

6. A rectifier consisting of one or more nanowires, each nanowire consisting of a purified protein filament isolated from a Geobacteraceae bacterium, the purified protein filament containing a single identifiable protein, wherein the rectifier is capable of operating as an asymmetric conductor and of establishing an electrical connection with an insoluble electron acceptor, wherein the single identifiable protein is encoded by a PilA polypeptide.

7. The rectifier of claim 6 wherein each of the single identifiable proteins are the same type of protein.

8. The rectifier of claim 6 wherein the insoluble electron acceptor is selected from Fe(III) oxide minerals, an electrode, a second purified pilus and combinations thereof.

9. The rectifier of claim 6 adapted for use in radio demodulation, low voltage AC-DC power conversion, current steering, power switches, over voltage protection, logic circuitry in electronic devices or computer chips.

10. The rectifier of claim 6 capable of functioning for voltages in a range of about ±0.8 V or a range of about ±1.2 V.

11. The nanowire of claim 1 wherein the PilA polypeptide consists of amino acids selected from SEQ ID Nos. 1 and 10-18.

12. The nanowire of claim 1 wherein the purified peptide subunits form an assembly having a main pilus with one or more junctions and one or more secondary main pili, wherein the main pilus has a length and said junctions are substantially perpendicular to said length.

13. The nanowire of claim 1 wherein the purified peptide subunits form a branched assembly containing a main elongated pilus having a length and a plurality of branch pili emanating from the main elongated pilus at one or more substantially fixed distances along said length.

14. The nanowire of claim 12 configured to form part of an apparatus.

15. The nanowire of claim 14 comprising more than one pilus, wherein the apparatus contains at least one junction therebetween.

16. The rectifier of claim 6 capable of conducting electrons laterally in a range of about ±1V or higher.

17. The rectifier of claim 6 wherein the PilA polypeptide consists of amino acids selected from SEQ ID Nos. 1 and 10-18.

* * * * *

UNITED STATES PATENT AND TRADEMARK OFFICE
CERTIFICATE OF CORRECTION

PATENT NO. : 8,729,233 B2  
APPLICATION NO. : 13/221459  
DATED : May 20, 2014  
INVENTOR(S) : Reguera et al.

Page 1 of 1

It is certified that error appears in the above-identified patent and that said Letters Patent is hereby corrected as shown below:

On the title page, item [56], Col. 1, Line 11: Delete "sulferreducens" and insert --sulfurreducens--

On the title page, item [56], Col. 2, Line 9: Delete "Michicgan" and insert --Michigan--

In the Specification

Col. 13, Line 42: Delete "kpa" and insert --kDa--

Col. 13, Line 44: Delete "kpa" and insert --kDa--

Col. 13, Line 48: Delete "kpa" and insert --kDa--

Col. 13-14, Table 1: Delete "pospho," and insert --phospo,--

Col. 20, Line 51: Delete "experiments" and insert --experiments.--

Col. 23, Line 43: Delete "(Spectrocell Inc.)" and insert --(Spectrocell Inc.).--

In the Claims

Col. 37, Line 26, Claim 4: Delete "claim 2" and insert --claim 3--

Signed and Sealed this
Twenty-third Day of September, 2014

Michelle K. Lee
*Deputy Director of the United States Patent and Trademark Office*